US009737382B2

(12) United States Patent
Morales et al.

(10) Patent No.: US 9,737,382 B2
(45) Date of Patent: Aug. 22, 2017

(54) APPARATUS AND METHODS OF MAKING DENTURE DEVICES

(71) Applicant: James R. Glidewell Dental Ceramics, Inc., Newport Beach, CA (US)

(72) Inventors: David Morales, Oceanside, CA (US); Gilbert A. Rivera, Santa Ana, CA (US); Nhung T. Truong, Anaheim, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 750 days.

(21) Appl. No.: 14/142,393

(22) Filed: Dec. 27, 2013

(65) Prior Publication Data

US 2015/0182314 A1    Jul. 2, 2015

(51) Int. Cl.
    *A61C 13/00*    (2006.01)
    *A61C 9/00*     (2006.01)
    *A61C 13/34*    (2006.01)

(52) U.S. Cl.
    CPC ...... *A61C 13/0004* (2013.01); *A61C 13/0019* (2013.01); *A61C 9/0053* (2013.01); *A61C 13/34* (2013.01)

(58) Field of Classification Search
    CPC . A61C 13/0004; A61C 13/0019; A61C 13/34; A61C 9/0053
    See application file for complete search history.

(56) References Cited

U.S. PATENT DOCUMENTS

| 7,153,135 | B1 | 12/2006 | Thomas |
| 8,043,091 | B2 | 10/2011 | Schmitt |
| 8,366,445 | B2 * | 2/2013 | Vuillemot .......... A61C 13/0004 433/213 |
| 2005/0181323 | A1 * | 8/2005 | Lauciello .......... A61C 19/10 433/26 |
| 2007/0287131 | A1 * | 12/2007 | Ruppert .......... A61C 13/0004 433/223 |
| 2009/0298017 | A1 * | 12/2009 | Boerjes .......... A61B 5/4547 433/214 |
| 2010/0038807 | A1 | 2/2010 | Brodkin et al. |

(Continued)

FOREIGN PATENT DOCUMENTS

| WO | WO2011100976 | 8/2011 |
| WO | WO2012045314 | 4/2012 |

(Continued)

OTHER PUBLICATIONS

Jacob, G. "Three-Dimensional Printing of Dentures Using Fused Deposition", Inside Dental Technology, Jul./Aug. 2013, vol. 4, Issue 8.

*Primary Examiner* — Kenneth M Lo
*Assistant Examiner* — Michael J Huntley
(74) *Attorney, Agent, or Firm* — Dianne Burkhard

(57) ABSTRACT

The present application describes a method for designing and manufacturing a denture device for a patient. A method is described for designing a virtual denture and manufacturing a functional fitting replica denture from the virtual denture. An apparatus comprising a functional fitting replica denture is prepared having denture teeth having a fit substantially similar to the final denture. The methods and apparatus described herein reduce the number of visits required to manufacture the final denture.

19 Claims, 12 Drawing Sheets

(56) References Cited

U.S. PATENT DOCUMENTS

| | | | |
|---|---|---|---|
| 2010/0151417 A1* | 6/2010 | Nilsson | G06F 19/3437 433/167 |
| 2010/0203478 A1* | 8/2010 | Rubbert | A61O 5/007 433/212.1 |
| 2011/0129796 A1* | 6/2011 | Riggio | A61C 9/0006 433/171 |
| 2011/0247214 A1* | 10/2011 | Huge | A61C 7/002 29/896.11 |
| 2011/0276159 A1* | 11/2011 | Chun | A61C 13/0004 700/98 |
| 2012/0015330 A1* | 1/2012 | Zhivago | A61C 13/0004 433/215 |
| 2012/0095732 A1 | 4/2012 | Fisker et al. | |
| 2012/0179281 A1* | 7/2012 | Steingart | A61C 13/0004 700/97 |
| 2012/0258430 A1 | 10/2012 | Ruppert et al. | |
| 2012/0284000 A1 | 11/2012 | Nilsson | |
| 2012/0308954 A1* | 12/2012 | Dunne | A61C 13/34 433/57 |
| 2012/0308963 A1* | 12/2012 | Hasselgren | A61C 8/0036 433/201.1 |
| 2013/0060532 A1* | 3/2013 | Clausen | A61C 13/0004 703/1 |
| 2013/0218531 A1 | 8/2013 | Deichmann et al. | |
| 2014/0162233 A1* | 6/2014 | Hultgren | A61C 13/34 434/270 |
| 2014/0170591 A1* | 6/2014 | El-Siblani | A61C 13/0004 433/36 |
| 2014/0272797 A1 | 9/2014 | Prestipino | |
| 2015/0111177 A1* | 4/2015 | Fisker | A61C 13/01 433/196 |
| 2015/0132718 A1* | 5/2015 | Kerschensteiner | A61C 13/01 433/196 |
| 2015/0140517 A1* | 5/2015 | Vuillemot | A61C 13/0019 433/226 |
| 2015/0238289 A1* | 8/2015 | Wouters | A61F 5/566 700/98 |
| 2016/0166362 A1* | 6/2016 | Nonboe | A61C 9/004 703/1 |

FOREIGN PATENT DOCUMENTS

| | | |
|---|---|---|
| WO | WO2012041329 | 5/2012 |
| WO | WO2012083959 | 6/2012 |
| WO | WO2013053903 | 4/2013 |
| WO | WO2013120955 | 8/2013 |
| WO | WO2013124452 | 8/2013 |

* cited by examiner

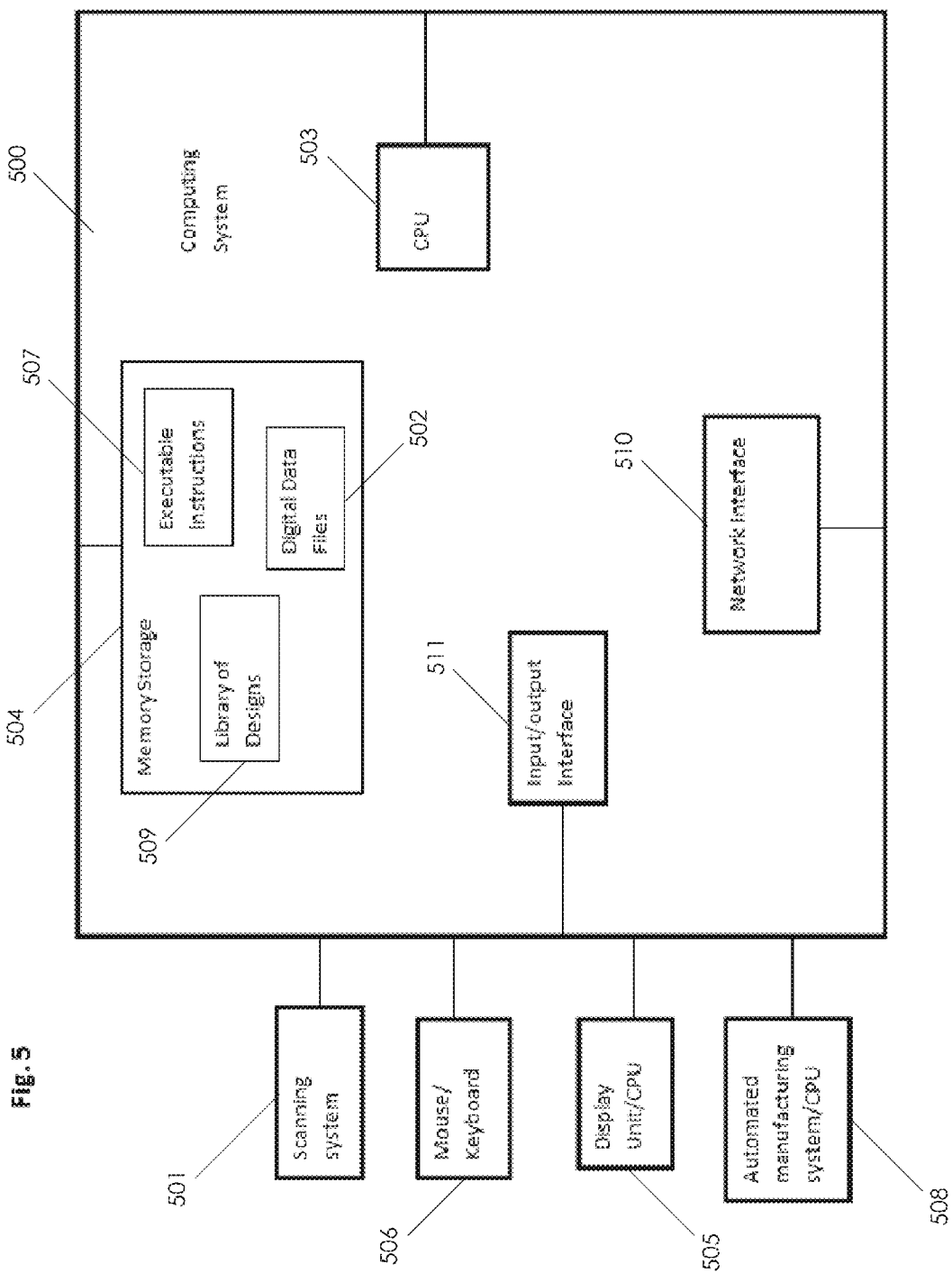

Fig. 12
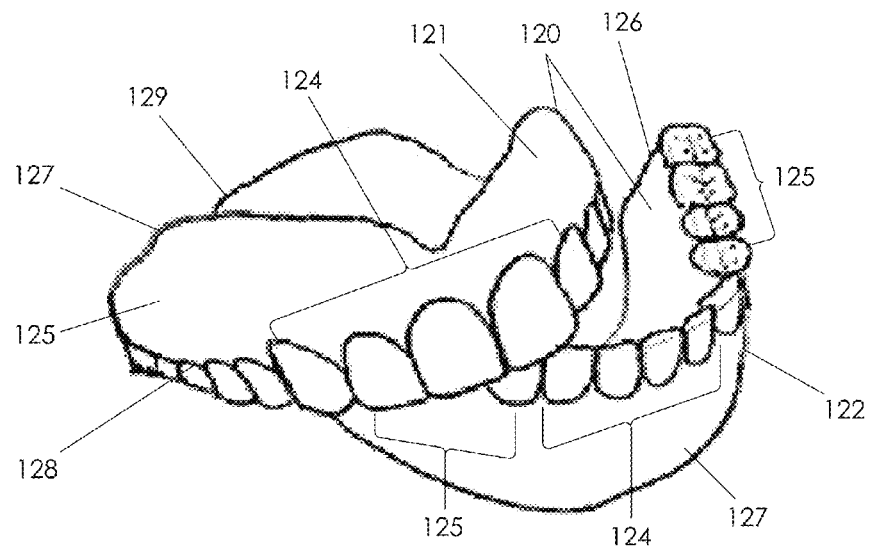
Fig. 13b
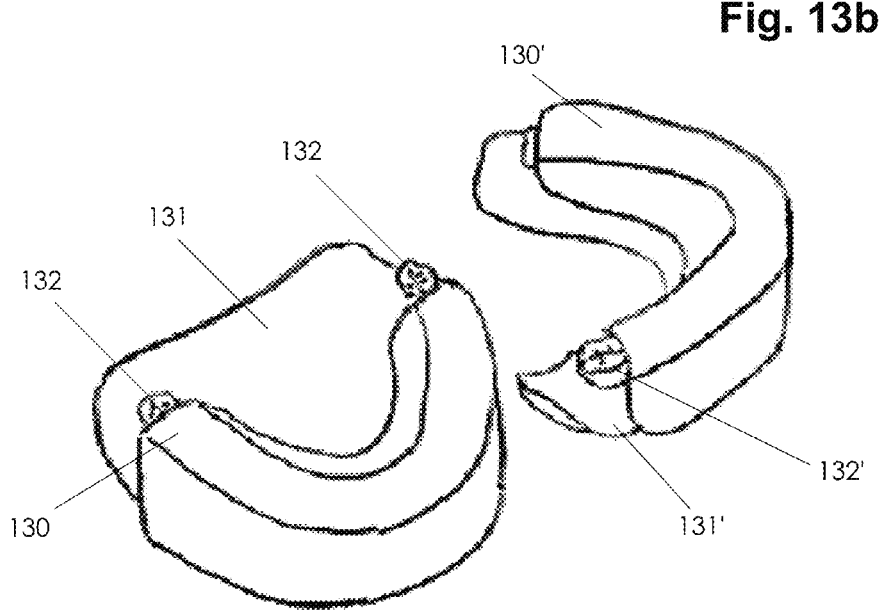
Fig. 13a

APPARATUS AND METHODS OF MAKING DENTURE DEVICES

BACKGROUND

Fabricating a well-designed denture set to replace missing teeth in an edentulous patient is both challenging and time consuming, requiring numerous visits between a patient and a healthcare professional. Moreover, impressions and models are sent back and forth between a healthcare professional and a dental laboratory to achieve a fit and aesthetics satisfactory to dentist and patient, impacting the time required to prepare the final denture.

Traditionally, patient visits are necessary to take impressions of a patient's edentulous ridge, to evaluate the fit of a try-in denture, to check the bite relationship of a try-in denture, and to ensure accurate fit of the final denture. In a first visit, an impression of a patient's oral anatomy is taken which is used by the dental laboratory to form a stone model of the patient's maxillae and mandible, providing information regarding features such as the size and shape of edentulous ridges. Optionally, custom trays may be made from the stone model for taking a final impression in a subsequent patient visit. In a further visit, a patient's bite registration is taken to determine the relationship between mandible and maxillae by inserting wax rims into the oral cavity of a patient. The bite registration information is sent to the dental laboratory for preparation of a try-in denture. The try-in denture is usually composed of a wax denture in which final denture teeth have been hand-set by a laboratory technician.

In further visit, the patient is examined with the wax try-ins for fit and appearance, and the health care professional notes any adjustments that may be required before preparation of the final denture. After all final adjustments are made, a dental laboratory prepares the final denture set based on the wax try-in. As a result of limitations in this process, sometimes the fit of the final denture is inadequate, requiring re-manufacturing of the dentures, repeating all or part of this process.

There is a need to reduce the expense and time required to prepare a final denture set. Savings in time and money can be achieved by reducing the number of visits between the patient and the healthcare professional, and reducing the time it takes the dental laboratory to make a final denture.

It is advantageous to make dentures by methods that reduce the limitations inherent in traditional manufacturing processes. Creating virtual designs by computer-aided design (CAD) methods is effective for reducing the time to make dental restorations. CAD designs complemented by the use of patient data are known for use in dental restorations. Digital patient data may be obtained directly from a patient's mouth by a handheld scanner, or from scan data of negative impressions, from stone models made from the impressions of a patient's mouth. Additionally, input from a virtual library of teeth shapes have been used in conjunction with patient data to create dental restorations. CAD design methods can enhance both the shape and function of the restoration. Optical and contact digitizers used to provide virtual data of a patient's oral anatomy are described in the literature, and some are commercially available.

CAD design used in conjunction with computer-assisted manufacturing (CAM) is known in dental restorations. Automated manufacturing processes include both subtractive and additive processes. Additive processes include those known by terms such as three-dimensional (3D) printing, additive manufacturing, rapid prototyping and rapid manufacturing, and include processes of forming a three-dimensional solid objects from a virtually designed digital model. Additive manufacturing processes, such as 3D printing, are distinct from machining or milling techniques that rely on removal of material by cutting or drilling (a substractive process).

In 3D printing, a virtual or digital representation of an object is reduced to a physical form by depositing material in a pattern corresponding to a cross-sectional layer of the object. Material which is sufficiently flowable, either as a liquid, or a solid that can be rendered flowable, may be formed layer by layer by a 3D printer. The flowable material is solidified and subsequent layers are formed thereon. Cross-sections of the virtual representation of the object are used to form each layer, for example, by moving a print head over a work piece and activating elements of the print head to create a layer of the object. Printing may be performed by any method known in the art to form layers that ultimately result in a solid object.

Where a liquid is used, a material such as a polymerizable liquid material is printed according to the digital representation. The liquid is hardened in the required pattern, for example by cross-linking, or where a molten thermoplastic material is used, by cooling. Upon sufficient hardening or crosslinking of a first layer, subsequent layers are printed and hardened. The liquid level is raised a short distance and the process is repeated. Each layer corresponds to a cross-section of the virtual representation and a cross-section of the object to be formed. In a further method, the liquid material may be applied as drops in a pattern according to the cross-sectional object to be formed.

In another method, powder is used, instead of liquid, to form the three-dimensional (3D) object. Powder, applied to a substrate in a pattern corresponding to a layer of a digital representation, is hardened by any known method suitable for the selected powder such as heating. Each layer of a 3D object may be created by spreading a thin layer of powder over the surface of a powder bed and hardened or partially hardened as each layer is laid down. Subsequent layers of powder are laid down in sequence upon coalescing of the initial layer to a stable form. Whether liquid or powder, material deposition is controlled by a computing device, such as a computer, personal computer, microcontroller, or the like.

Automated manufacturing processes, used in combination with virtual design process, standardize the manufacturing process and realize both time and cost savings in dental restoration production.

SUMMARY

The present invention describes a method for designing and manufacturing a final denture for a patient. A method is also described for designing a virtual denture, as well as a method for manufacturing a functional fitting replica denture from the virtual denture. An apparatus is described that comprises a functional fitting replica denture made from a physical model of the virtual denture with actual denture teeth positioned in the physical model. Also described is a method for making the functional fitting replica denture that reduces the number of steps taken to manufacture a final denture. Further described is an apparatus for determining the vertical dimension of occlusion in a patient.

In accordance with methods described herein, a virtual denture is designed via CAD methods combining information from a patient's oral anatomy and a virtual denture teeth design. Described herein is a plurality of virtual denture teeth designs wherein each design has a teeth set that is prearranged in a fixed position in an occlusal scheme corresponding to a specific arch shape and a specific size. The plurality of virtual denture teeth designs have been designed based on an analysis of measurements of accumulated data from previously made dentures. Thus, automatic generation of a virtual denture design may be achieved based on similarities between a new patient and designs provided for in the library. Methods for designing virtual dentures include the step of selecting a virtual denture teeth design from a plurality of designs that correspond to the size and shape of the patient's oral anatomy.

The method for designing the virtual denture comprises accessing data of the patient's oral anatomy, such as size and shape of the patient's maxillae and mandible, to select a pre-designed virtual denture teeth design from a plurality of designs, thereby automatically generating a design that fits the size and shape of the patient's oral anatomy. It is advantageous that a virtual denture can quickly achieved by selecting a pre-designed virtual denture teeth design that is compatible with the size and shape of the patient's oral anatomy.

Once completed, the virtual denture defines parameters that are used in automated manufacturing processes to form a physical model of the virtual denture. Additional parameters specific to the individual patient, such the topography of gingiva and characteristics of the soft palate, can be incorporated into the virtual design to enhance the fit and appearance denture. These features, formerly traditionally designed by hand by a laboratory technician, can be virtually designed and translated directly to a physical model, for example, by an additive manufacturing process.

The physical model can be modified by the addition of denture teeth in one or more regions to make a functional fitting replica denture. A method is described for making a functional fitting replica denture that has actual denture teeth precisely aligned in a formable material replicating the placement of teeth from the virtual denture. A functional fitting replica denture made by setting teeth and forming a gingival architecture by automated processes can achieve a better fit than a typical try-in denture by accurately replicating the unique characteristics of the patient. Unlike traditional methods of forming a try-in, which include manual or hand-setting of denture teeth and the manual wax-up of the gingival part by a technician, automated processes are precise, repeatable and accurately reflect the features of a patient's oral anatomy. In contrast to a traditional try-in denture, the functional fitting replica denture can be used to accurately check bite registration. Because it is functional, the patient can bite and/or chew with the device in place without destruction of the set-up or crushing of the wax used in traditional try-ins. Moreover, the functional fitting replica denture replicates the fit and structure of the gingival portions of a final denture with regard to size and shape, as well as the occlusal scheme and alignment of the final teeth.

Further described herein are methods for using a functional fitting replica denture to obtain bite registration data. Traditional materials used in obtaining bite registration data include using a pair of wax bite rims that is bulky and does not fit well within a patient's oral cavity, often resulting in inaccurate measurements. Methods for obtaining bite registration data are described herein that increase the accuracy of the data by replacing an upper and/or lower bite rim materials with an upper and/or lower functional fitting replica denture made by the described methods. Methods for obtaining bite registration data result in more accurate vertical dimension of occlusion and bite registration measurements.

As used herein, a denture device includes one or more of a final denture (full denture or partial denture), a physical model of a denture, a functional fitting replica denture, or an apparatus for bite-registration. The physical model of a denture describes an apparatus that has been constructed by any process, including and not limited to methods known by the terms subtractive manufacturing, additive manufacturing, rapid prototyping, rapid manufacturing, three-dimensional printing (3D printing), stereo lithography, and the like. The term functional fitting replica denture describes an apparatus constructed from the physical model by methods mentioned above, that has been further processed to include actual denture teeth. Denture teeth describe actual artificial denture teeth that are typically used in a final denture restoration. The terms physical model of a denture, functional fitting replica denture, denture device, final denture and an apparatus for bite registration, are intended to optionally include an upper portion for insertion onto the maxillae of a patient, a lower portion for insertion onto the mandible of a patient, or a denture device comprising both an upper portion and lower portion.

BRIEF DESCRIPTION OF THE FIGURES

FIG. 5. A block diagram of a computing system according to one embodiment described herein.

FIG. 12. A view of one embodiment of a physical model described herein.

FIGS. 13a and 13b. A view of one embodiment of a mold on a physical model described herein.

While the above-identified figures set forth embodiments described here, other embodiments are also contemplated, for example, as described in the detailed description. The figures presented are illustrative representations of embodiments, and numerous other modifications and embodiments can be devised by those skilled in the art that are within the scope of the disclosure.

DETAILED DESCRIPTION

Figure 1:
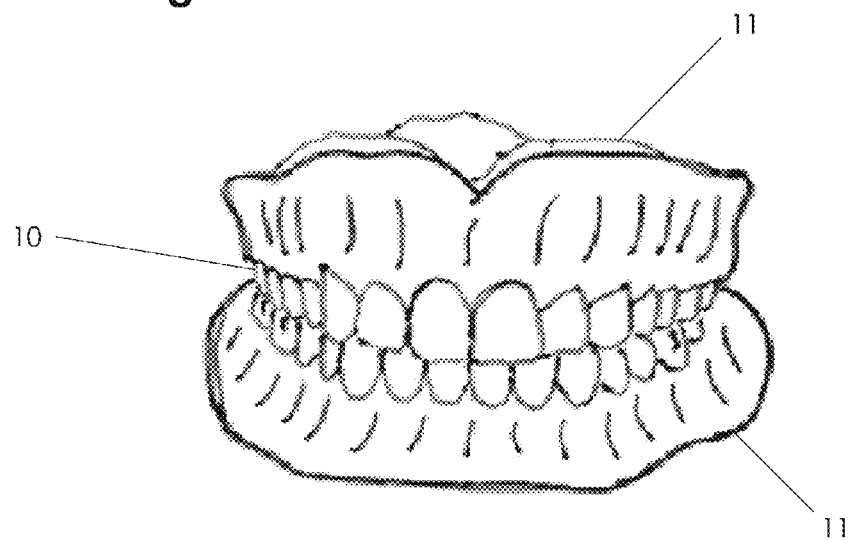
FIG. 1. A denture device according to an embodiment described herein.
Figure 3:
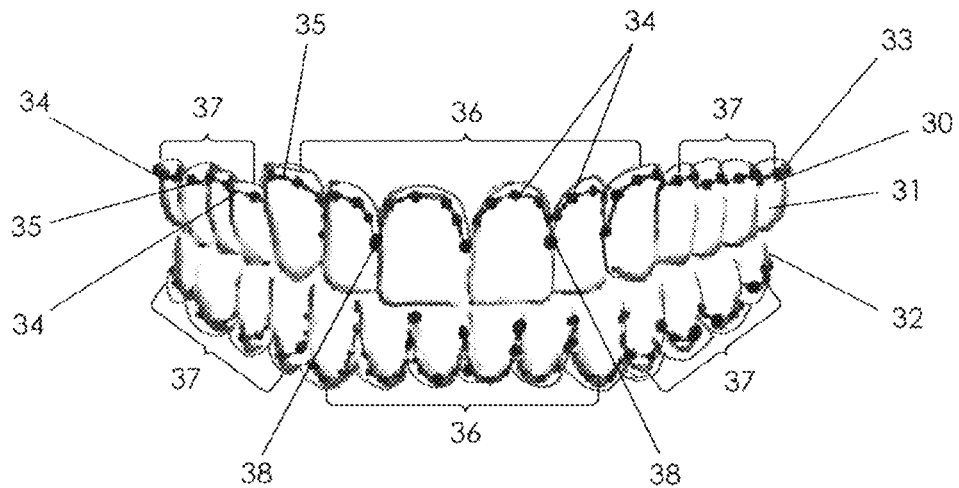
FIG. 3. A virtual denture teeth design and virtual gingival boundary according to one embodiment.
Figure 4:
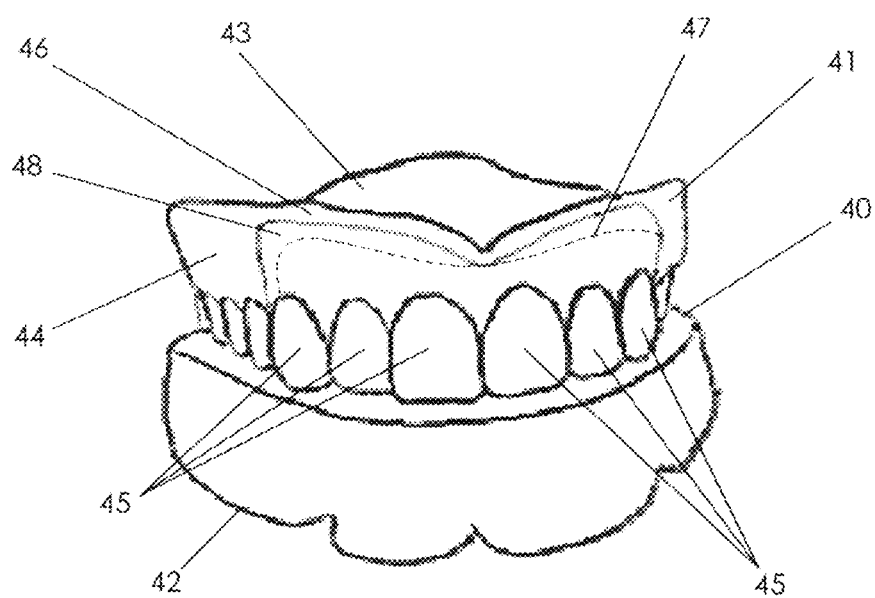
FIG. 4. A bite registration apparatus according to an embodiment described herein.

A method for making a denture device for placement on the edentulous ridge of a patient is described. As illustrated in FIG. 1, a denture device (10) comprises an upper denture (11) for placement on a patient's maxillae, a lower denture (11) for placement on a patient's mandible, or both an upper and lower denture. A functional fitting replica denture, illustrated in FIG. 2, used for trying in the mouth of a patient prior to making the final denture, is also described. In one embodiment, a virtual denture teeth design (as exemplified in FIG. 3) is designed via CAD methods. The virtual denture teeth design and information regarding the patient's oral anatomy is combined by methods described herein to make a virtual denture that is used for making a denture device. Further described, as illustrated in FIG. 4, is a bite registration device made by methods described herein.

In accordance with the methods set forth, the virtual 3D representation of a patient's oral anatomy may be obtained by taking an image of at least a part of the patient's oral cavity, including the patient's maxillae, the patient's mandible, or both the maxillae and the mandible. Image data may be collected on the entire arch, or just a portion of one or both arches. Image data is converted to a computer generated virtual model of a 3D representation of a patient's present oral anatomy, and is recorded in a data record according to known methods. Information relating to a edentulous patient's maxillae and/or mandible may be obtained that includes the shape and size of the maxillary and/or mandibular arches, bite relationship details of soft tissue and/or gingiva which includes characteristics such as gingival size, shape and texture, characteristics of inner and outer gingiva, and palatal characteristics. When these features are incorporated into the virtual denture, a functional fitting replica denture or final denture may be obtained having an accurate size, a secure fit onto the patient's maxillae and/or mandible, and realistic aesthetics.

Images may be taken and recorded by known methods for obtaining, recording and converting 3D patient information into digital data files suitable for creating a computer generated virtual 3D representation of the patient's oral anatomy. A three-dimensional camera, a computerized tomography apparatus, and hand held scanning devices for scanning a patient's oral cavity may be used. Scanning systems known for obtaining information from the patient's oral anatomy include IOS Technologies FastScan® intraoral and impression scanning systems, iTero® scanning system (Align Technologies), ESPE True Definition Scanner (3M), and 3Shape D640 scanner.

Scan data may also be obtained from a negative impression of a patient's maxillae and/or mandible, or from a stone or plaster model made from the negative impression by known techniques. A negative impression may be made, using a material placed in the oral cavity usually via dental impression trays. Materials for making negative impressions include sodium alginate, polyether and silicones including condensation cured silicones and addition-cured silicones, including polyvinyl siloxane (PVS). A scan of the negative impression can be provided, for example, as an array of negative image scan data generated by a scanner.

Positive image scan data may also be used, either in addition to, or alternatively to, other scan data. Positive image scan data is typically obtained from a stone or plaster model derived by casting the negative impression of the patient's maxillae and/or mandible. The stone or plaster model can be made by pouring a casting material, such as gypsum or plaster, into the negative impression. After setting, the stone or plaster model can be scanned. The stone model may be digitized by known scanning systems, such as laser scanning, optical scanning, destructive scanning CT scanning and sound wave scanning, to obtain a digital arch model. The stone model can also be used to determine bite registration by alignment for example, in a dental articulator. The alignment also can be done virtually, with an articulator from a software program.

A bite registration apparatus may be used to obtain additional information, such as vertical dimension of occlusion and bite classification (for example, Class I, II or III). Scan data may be obtained from bite registration apparatus and the data may be used to spacially orient the maxillae and or mandible relative to one another. In a further option, data may also be obtained from previously made dentures, for example, where a replacement set of dentures is needed. To obtain patient information, previously made dentures may be scanned by any suitable method discussed herein, such as by a desk top scanning device.

The scan system may provide digital data records of portions of the patient's oral anatomy to a computing system. The digital data may be converted from digital point clouds to 3D representations, for example 3D surfaces, by means of software such as Geomagic Wrap® software (by Geomagic, Inc.) With reference to the diagram of FIG. 5, in accordance to one embodiment, a computing system (500) is provided in which the scan data, obtained by a scanning system (501) and converted to a digital data record, is uploaded as a digital data file (502) to the computing system by a central processing unit (CPU) (503) and saved in a memory storage device (504). Where scan data from a negative impression is used, software that is part of the scanning system or the computing system (500) may convert the scan data to a positive image for display on a display unit (505) of a computing system (500). Negative scan data converted to a positive image by software and provided to CPU (503) may be saved as a permanent digital data file (502) in a memory storage device (504).

The computing system (500) may further comprise a user input device (506) such as a mouse or keypad, and modem. Commercially available software packages may be stored in a memory storage device (504) and providing executable instructions (507) to be executed by the CPU (503) to generate virtual 3D representations of the patient's oral anatomy from the scan data. The virtual 3D representation is obtained and recorded in a digital data file according to known methods. The computing system (500) may be a special purpose computer or a personal computer comprising available software packages, and the display unit (505) may include any known suitable display device such as LCD displays.

In one embodiment, digital data files from more than one patient image are provided to form a digital data record of the patient's oral anatomy. A computing system (500) having software that can provide executable instructions to overlap and/or register images is used to assemble the plurality of scans into a computer-generated three dimensional representation of the oral cavity. Available software may be selected or developed that has instructions for overlapping and registering the data from multiple scans, to provide digital registration data of the multiple scans to be used in designing a virtual denture (30) model and/or a virtual denture (FIGS. 6a-10). In one embodiment, scan data from the patient's maxillae and/or mandible, and/or bite registration is combined by software package to provide a complete digital data record of the patient's oral anatomy.

Virtual Denture Teeth Designs

Described herein is a method of making a plurality of virtual denture teeth designs. With reference to FIG. 3 virtual denture teeth designs (30) have upper and lower portions of a teeth set (31, 32) prearranged in a fixed position in an occlusal scheme corresponding to an arch shape and size. A plurality of pre-designed virtual denture teeth designs in a variety of arch shapes and sizes may accommodate a majority of patient cases without requiring time-consuming adjustments to the position of individual teeth, or to the arrangement of teeth around an arch, or modifications to size of the design. By providing a plurality of pre-designed virtual denture teeth designs, the number of steps required to design a virtual denture is reduced, when compared to known methods. Because virtual denture teeth designs are pre-designed, the method step of designing a plurality of virtual denture teeth designs is a separate method step from the step of designing the virtual denture which incorporates patient-specific data.

A computer-aided design (CAD) method for creating virtual denture teeth designs is described. In one embodiment, a user interface of a computer system (500) may be used to actuate executable instructions (507), for example, for viewing a library of teeth and selecting virtual teeth of a specific size and shape from a library of teeth, and arranging the virtual teeth in an arch shape to conform to a particular arch shape and size to form a virtual denture teeth design. Referring to FIG. 5, the virtual denture teeth designs may be designed via a design restoration software program in a CAD system suitable for virtual dental design by use of a computing system (500) and a system input and output interface (511). Software programs for designing dental restorations are known by designers of dentures and other dental restoration technicians, and provide executable instructions (507) for use on a computing system (500). CAD software packages commercially available (such as, 3Shape Dental Designer™ program, and NetFabb® Software) may be used to generate and/or virtual denture teeth designs in a multiplicity of arch shapes and sizes that can be stored as digital data files of a design library (509) on a memory device (504).

In another embodiment, virtual denture teeth designs may be made by scanning a multiplicity of actual pre-made denture set-ups that have been created in specific sizes and arch shapes designed to fit a majority of denture patients. In one embodiment, the denture set-ups may comprise a multiplicity of actual final dentures made for patients in a variety of sizes and arch shapes. In a further embodiment, the pre-made denture set-ups may be made by creating designs of a variety of arch shapes, sizes, and teeth alignments and orientations, and forming wax set-ups with denture teeth set in wax according to the particular designs. The wax set-ups may be cast as stone models from which image data of the models may be obtained. Images of the pre-made denture set-ups may be taken, for example, by known scanning methods to form digital data files of the denture set-ups. In one embodiment, for example, the pre-made denture set-ups are scanned by a desktop scanner to form digital data files in a .dcm format, that can be converted, for example, into an .stl format, to create virtual computer generated 3D representations of the virtual denture teeth designs by known software programs (such as 3Shape Dental Designer™) The method of scanning denture set-ups may be by any known method of scanning, as described herein, that is suitable for creating digital data files that can be converted to virtual 3D representations.

In a further step, the virtual 3D representation of the multiplicity of scanned denture set-ups can be modified by design software programs to optimize the virtual denture teeth designs. In one embodiment, denture design software tools can be used to virtually remove scanned gingival regions of the pre-made denture set-ups. Thus, in one embodiment, the virtual gingiva regions from the pre-made denture set-ups are removed leaving only the virtual denture teeth set in a specific alignment and orientation. The resulting virtual 3D representations comprise a plurality of pre-designed virtual denture teeth designs (30) that comprises teeth sets (31, 32) prearranged in a fixed position in an occlusal scheme corresponding to an arch shape and size. By eliminating scanned gingival regions of the pre-made denture set-ups, patient specific data can be incorporated into the new virtual denture design to replicate the patient's gingival architecture. Digital data files (509) of the virtual denture teeth designs may be added, for example, to a virtual library of an existing dental restoration software that is suitable for use in designing a virtual denture. In one embodiment, a non-transitory computer readable medium is provided having one or more computer instructions stored thereon, wherein the computer instructions comprise instructions for execution on a computing system for carrying out a method of designing a plurality of virtual denture teeth designs as described herein.

Figure 6A:
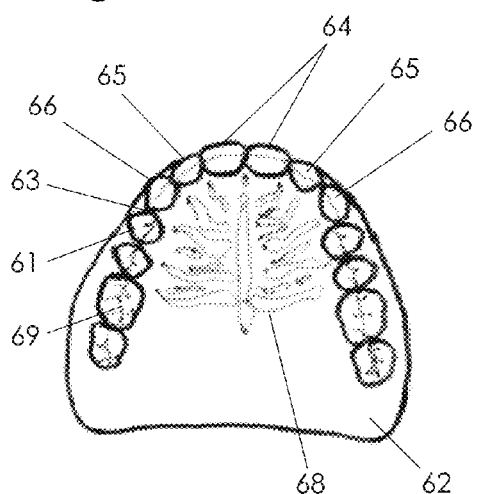
FIGS. 6a-6d. A virtual denture according to one embodiment described herein.
Figure 6B:
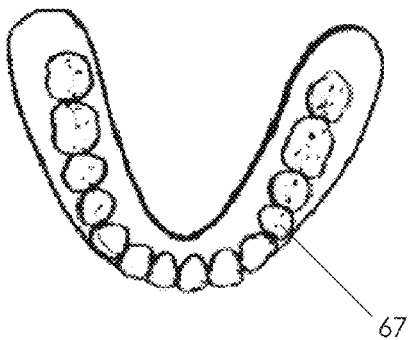
Figure 7A:
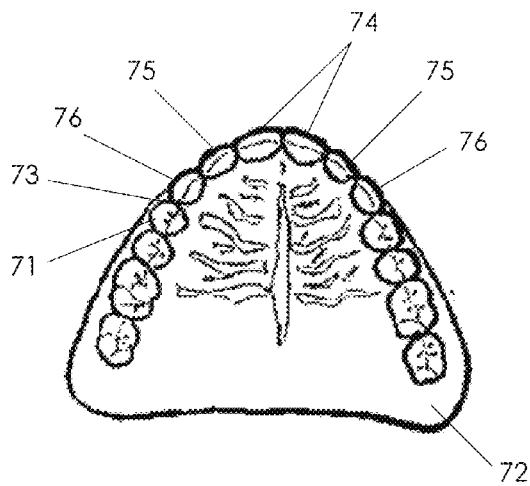
FIGS. 7a-7c. A virtual denture according to one embodiment described herein.
Figure 7B:
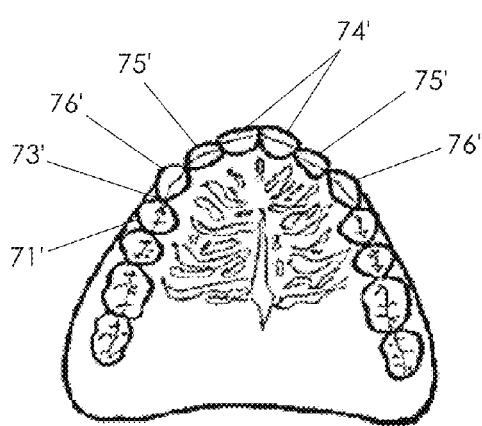
Figure 7C:
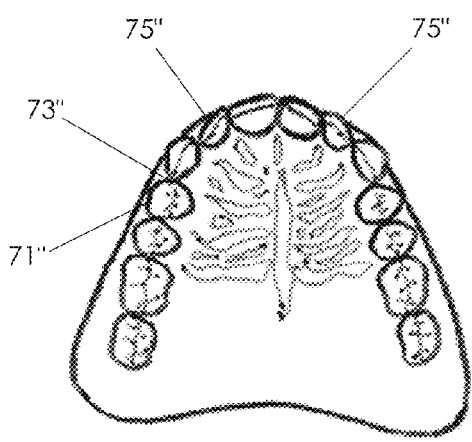
Figure 8A:
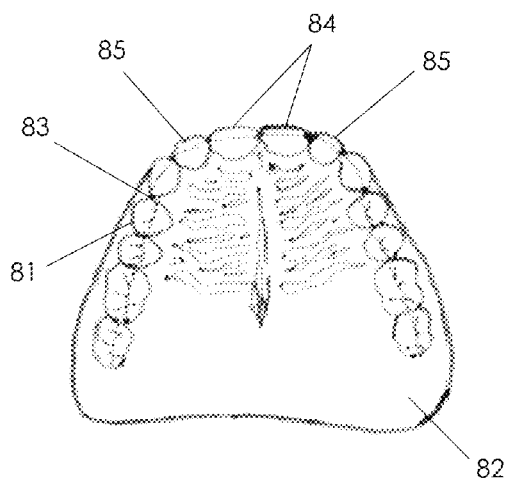
FIGS. 8a-8c. A virtual denture according to one embodiment described herein.
Figure 8B:
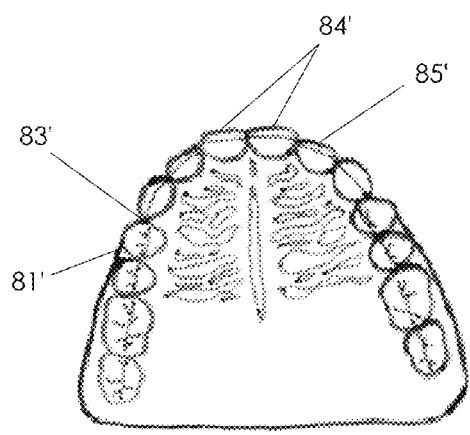
Figure 8C:
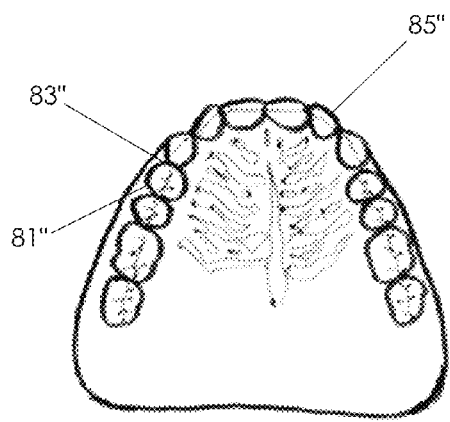

In one embodiment, as exemplified in FIGS. 6a and 6b, upper and lower portions of a virtual denture teeth design (61 and 67) are created having a virtual teeth set (63) in a prearranged fixed position corresponding to the ovoid shape of an arch. In another embodiment, as illustrated in FIG. 7a, a pre-designed upper virtual denture teeth design (71) is created having the virtual teeth set (73) prearranged in a fixed position corresponding to the tapering shape of an arch. In a further embodiment, FIG. 8a illustrates a pre-designed upper virtual denture teeth design (81) and virtual teeth set (83) that is prearranged in a fixed position on a virtual ridge (82) corresponding to a square arch shape. The virtual teeth sets may be pre-arranged in occlusal schemes according to additional arch shapes, as well as arch shapes that combine features of ovoid, square and tapering, such as a square-ovoid arch shape and a tapering-square arch shape.

In one embodiment, the computer executable instructions for forming virtual denture teeth designs comprises instructions for selecting and applying teeth from a digital library in a pre-arranged, fixed position, and arranging the virtual teeth in an occlusal scheme that corresponds to a shape of an arch selected from ovoid, tapering, and square. In another embodiment, the method for making a virtual denture teeth design comprises obtaining digital data files of scanned pre-made denture set-ups having teeth set in fixed positions in an occlusal scheme corresponding to a plurality of arch shapes, for example, ovoid, tapering and square; converting the digital data files into a virtual 3D representations; and modifying the virtual 3D representations by removing the virtual gingival regions to provide a virtual denture teeth design.

In a further embodiment, to provide for enhanced aesthetics, virtual denture teeth designs are created that have subtle differences in the alignment of teeth relative to each other, while still conforming to the overall arch shape. Teeth arrangements, such as an ideal arrangement, a masculine arrangement, or a feminine arrangement, can be selected to achieve a look that is pleasing to the patient. A method for making virtual teeth designs is provided that comprises providing computer executable instructions for arranging teeth in an arrangement having subtle differences in the alignment of teeth relative to each other, while still conforming to the overall arch shape. In a further embodiment, a method comprises forming virtual denture teeth designs by selecting a plurality of pre-made dentures comprising subtle differences in the alignment of teeth relative to each other, and forming pre-designed virtual denture teeth designs from the pre-made dentures as described above.

Figure 6C:
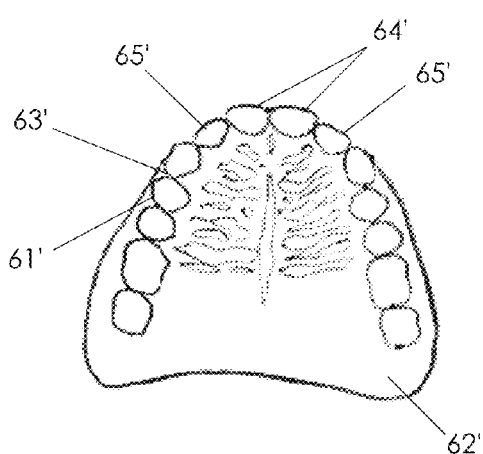
Figure 6D:
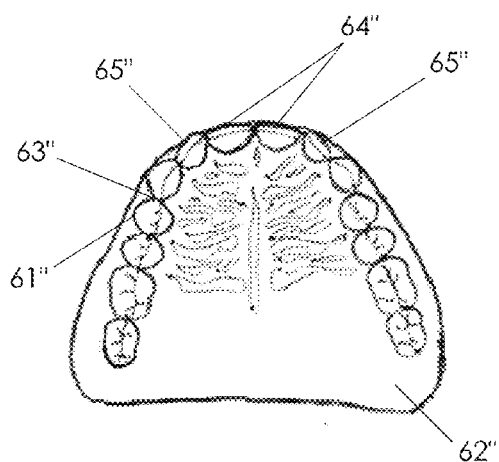

With reference to FIGS. 6a, 6c and 6d, the virtual denture teeth designs (61, 61', and 61"), which are shown on virtual arches (62, 62', and 62"), comprise an ovoid shape with the virtual teeth set pre-arranged in an ideal arrangement, a masculine arrangement, and/or a feminine, respectively. An ideal arrangement corresponding to an ovoid arch shape, as exemplified in FIG. 6a, may comprise upper central incisors (64), lateral incisors (65), and cuspids (66) set to a full curve around the arch. In another embodiment with reference to FIG. 6c, the virtual denture teeth design (61') comprises an ovoid shape, wherein the prearranged teeth set (63') is aligned in a masculine arrangement. A masculine arrangement of a teeth set may comprise central incisors (64') that are wider than the teeth of an ideal arrangement, The masculine arrangement may comprise central incisors in a substantially linear arrangement, with outward rotation at the distal, and/or lateral incisors (65') having a mesial rotation relative to the central incisors (64'). In another embodiment with reference to FIG. 6d, the virtual denture design (61") comprises an ovoid shape, with a virtual teeth set (63") in a feminine arrangement. A feminine arrangement of the virtual teeth may comprise central incisors (64") that are less wide than in an ideal arrangement, in substantially linear arrangement or with a slight mesial rotation, and/or lateral incisors (65") with an outward mesial rotation.

With reference to FIG. 7a, the virtual denture teeth design (71) that is shown on a virtual arch (72), comprises a tapering shape. The virtual teeth set (73) is pre-arranged in an ideal arrangement. In an ideal arrangement corresponding to a tapering arch shape, the central incisors (74), lateral incisors (75) and canines (76) may be arranged on an arch having a curve that converges to a point midline between the central incisors. In a further embodiment with reference to FIG. 7b, the virtual denture teeth design (71') comprises a tapering shape with the teeth set (73') in a masculine arrangement, and may have slightly larger central incisors (74') or canines (76'). The lateral incisors (75') may have a slight distal rotation. In a further embodiment with reference to the virtual denture teeth design (71") shown in FIG. 7c, the virtual teeth set (73") is in a feminine arrangement, having lateral incisors (75") with an outward mesial rotation.

With reference to FIG. 8a, the virtual denture teeth design (81) shown on a virtual arch (82) comprises a square shape, and the pre-positioned virtual teeth set (83) is pre-arranged in an ideal arrangement. In an ideal arrangement of a square arch shape, the central incisors (84) and/or the lateral incisors (85) may be substantially in linear arrangement. In a further embodiment with reference to FIG. 8b, the virtual denture teeth design (81') comprises a square shape, and virtual teeth set (83') is in a masculine arrangement. The central incisors (84') may be larger or more square in shape than in an ideal arrangement, and the central incisors (84') may be rotated outwardly at the distal, and the lateral incisors (85') may be rotated inward relative to the central incisors (84'). In a further embodiment with reference to FIG. 8c, the virtual denture teeth design (81") comprises a square arch shape, and virtual teeth (83") are in a feminine arrangement. In a feminine arrangement, the teeth may have a slight distal rotation of the lateral incisors (85") toward the distal.

Figure 9:
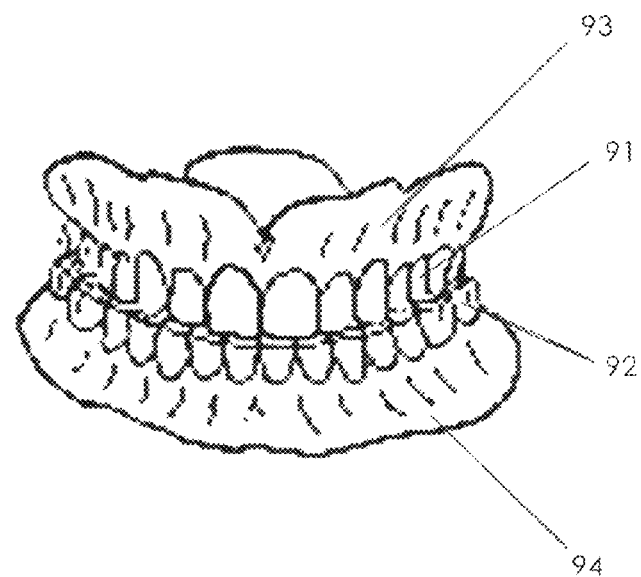
FIG. 9. A virtual denture according to one embodiment described herein.
Figure 10:
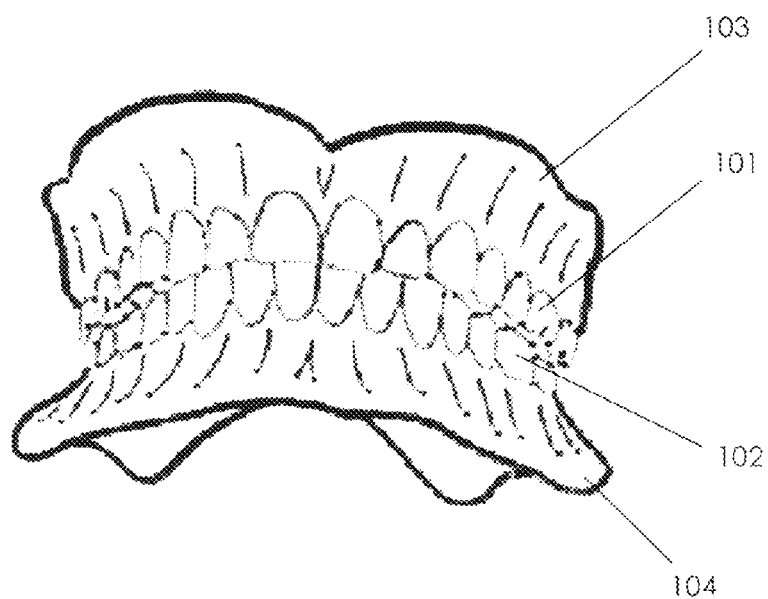
FIG. 10. A virtual denture according to one embodiment described herein.

In FIG. 9, a predesigned virtual denture teeth design, shown in occlusion on upper and lower virtual arches (93 and 94, respectively), is in a cross-bite configuration having upper (91) and lower (92) teeth sets. In this embodiment, a lower virtual teeth set (92) is positioned in buccal version to the upper virtual teeth set (91) when upper and lower arches are in occlusion. In a further embodiment, as exemplified in FIG. 10, a pre-designed upper (101) and lower (102) virtual denture teeth design is shown in a lingualized occlusion configuration on upper and lower virtual arches (103 and 104, respectively). In this embodiment, in occlusion the lower virtual teeth set (102) is positioned lingually relative to the upper virtual teeth set (101).

With reference to FIG. 3, pre-designed virtual denture teeth designs (30) each comprise upper and lower teeth sets (31, 32), and may be further designed to comprise a virtual gingival boundary line (33) that is specific to each virtual denture teeth design. The computing system may comprise software having executable instructions for providing of a number of virtual points (34) to be placed on the virtual teeth of the virtual denture teeth design. The computer executable instructions of the software program are adapted to map a number of reference points (34) on the virtual teeth set and create a line (35) that intersects the points on adjacent teeth, forming the virtual gingiva boundary line. In one embodiment, interproximal points (38) are located between teeth to facilitate forming a continuous gingival boundary line that traverses adjacent teeth, and upon execution of computer instructions, forms a virtual gingiva that, for example, extends over the interproximal space of the teeth, and/or or forms virtual interdental papillae. In one embodiment, the executable instructions are adapted to locate multiple points on the virtual teeth set and intersect the points to form a virtual gingiva boundary line that traverses the interproximal space of adjacent teeth, and that is continuous throughout the entire virtual set of teeth, in a single step. The virtual gingiva boundary line establishes a region where virtual gingiva will be automatically generated via executable computer instructions when integrated with the digital data of the patient's oral anatomy, without having to manually draw a virtual gingiva line on individual teeth, or each set of teeth every time a virtual denture is created. In one embodiment, the generated gingival boundary line continuously traverses substantially all of the teeth of the virtual denture teeth design. In another embodiment the gingival boundary line is on at least a portion of the teeth of the virtual set. In another embodiment, the virtual gingival boundary line continuously traverses multiple teeth, such as the teeth of the anterior teeth region (36), the posterior teeth region (37), a portion of the anterior teeth region, or a portion of the posterior teeth region, and generates a virtual gingiva that incorporates patient specific gingival architecture.

As mentioned above, the plurality of virtual denture teeth designs has multiple sizes of the same arch shapes to accommodate the needs of multiple patients having a variety of arch sizes. The multiplicity of sizes accommodate differences in molar-to-molar distances, canine-to-canine distances, vertical dimensions of occlusion, and/or measurements of front to back distances (as measured, for example, as the distance between the incisive papillae in the front and a central point between molars in the back of the mouth). To accommodate differences in arch sizes, a plurality of virtual denture teeth designs may be pre-designed with teeth having a selected width that is suitable to accommodate a specific arch size. To accommodate differences in vertical dimension of occlusion (VDO), a plurality of virtual upper and lower denture teeth designs may be created by selecting teeth having a length suitable to accommodate a specific VDO.

The virtual denture teeth design as described herein, may be created by developing computer executable instructions for selecting virtual teeth having a specific size and shape, and for arranging virtual teeth into the designs, or by use of a known software program for designing dental restorations. Once formed, the designs may be saved in a three-dimensional digital data file format, such as .stl. The virtual teeth sets may be designed by selecting teeth having a specific tooth size and shape from a digital library of a computer software program for designing dental restorations, or from a known manufacturer of denture teeth. Where the virtual denture teeth designs are created by selection of pre-made denture set-ups in a variety of sizes, the virtual denture teeth set correspond to the specific denture teeth size and shape that was selected when the pre-made denture set-ups were originally formed. Denture teeth are constructed having a specific size, form, shape, and color. Each tooth may be indicated by a mold number providing consistency in size and form, and therefore virtual denture teeth designs may comprise teeth corresponding to specific mold numbers as provided for by the denture teeth manufacturer, such as Kenson® denture teeth (distributed by Myerson LLC, Chicago, Ill.) or VITA Vident® denture teeth (Vident, Brea, Calif.). Virtual denture teeth designs are shown with teeth characteristics such as pits (69).

The virtual denture teeth designs may comprise posterior and anterior teeth, and may comprise a complete set of virtual teeth required for a final denture. Anterior teeth and anterior teeth region refers to the teeth in the front of the mouth, specifically the central incisors, lateral incisors, and cuspids (canines) of the maxillae and mandible. Posterior teeth and posterior teeth regions refer to the teeth that are posterior to the anterior teeth on the maxillae and mandible, for example, the first bicuspids, second bicuspids, first molars, and second molars.

In designing a plurality of virtual denture teeth designs, previously made actual dentures were analyzed and compared to patient data to form a plurality of designs that would accommodate a multiplicity of patient cases without requiring individual positioning or adjustment of separate teeth.

Virtual Denture

Observations and/or measurements from the patient's oral anatomy, as well as the patient's gender, are useful to select an appropriate pre-designed virtual denture teeth design from among the plurality of pre-made designs. Measurements of patient data are taken to select the virtual denture teeth design that has the greatest correspondence in arch size and arch shape, and bite relationship, from the plurality of virtual denture teeth designs. Patient data may be obtained, for example, from an actual or scanned impression, stone model, or existing dentures, or a scan of the patient's mouth, and include measurements that are typically obtained in traditional denture manufacturing processes. Patient information useful in selecting a virtual denture teeth design include measurements of a patient's edentulous ridge, for example, the molar-to-molar distance (e.g., the distance between second molars) of the mandible when measured straight across the arch, and similarly the distance between maxillary tuberosity of the maxillae, canine-to-canine distance, distance between incisive papilla and the center line between the molars, and the vertical dimension of occlusion of the mandible and maxillae. In one embodiment, the selection of a virtual denture teeth design may be based on the measurement of maxillary tuberosity distance of the upper edentulous ridge of a patient and the vertical dimension of occlusion.

Figure 11:
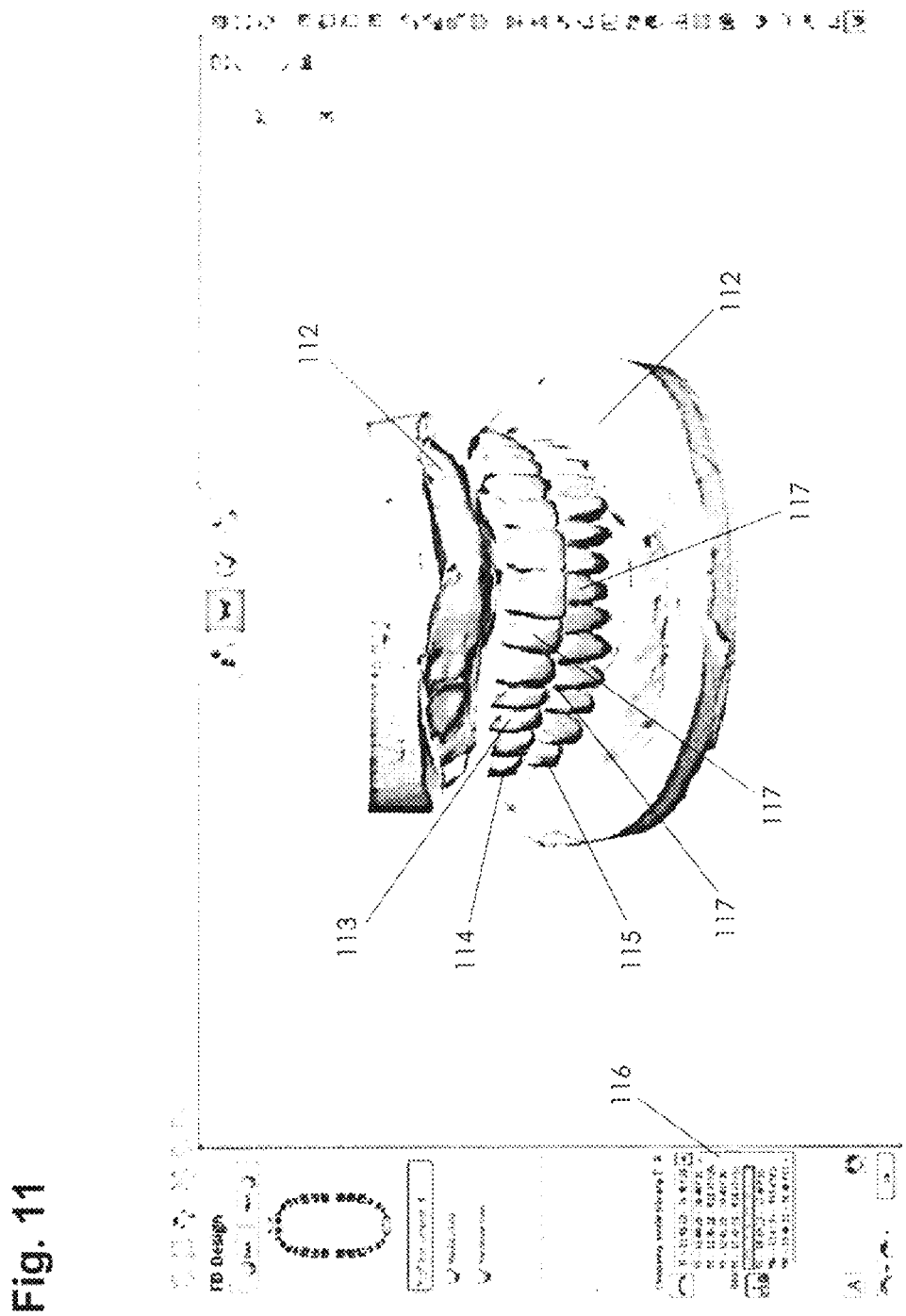
FIG. 11. A screen view of one embodiment of a virtual denture teeth design and a 3D representation of a stone model of a patient's oral anatomy according to an embodiment described herein.

A screen shot from a display unit, displaying an image and tools from a software program used for forming a virtual denture is illustrated in FIG. 11. A screen shot depicts an image of a 3D representation (112) of a scan of a stone model of a patient's oral anatomy, stored as a digital file on a computer system memory device. When the image is shown on the display unit, a gingiva region may be created over the area corresponding to the virtual arch, using tools of a software program. A virtual denture teeth design (113) stored as a digital file in a design library in a memory device is also shown. The virtual denture teeth design (113) may be selected from a plurality of designs (116) through user interface tools usable by execution of instructions provided by a software program. The 3D representation of the patient's oral anatomy and the virtual denture teeth designs may be aligned, for example, by a known dental restoration software program having executable instructions for transferring digital patient data to a virtual dental restoration. CAD dental restoration software, such as the software program used for virtual dental restorations may be used to apply and align the virtual denture teeth design (113) to the patient's ridges shown on the stone model (112). Each virtual denture teeth design comprises upper and lower regions (114, 115) in fixed occlusion, that move as a single unit. A software program having tools functioning through executable instructions may be used to rotate the virtual denture teeth design if necessary to provide appropriate alignment with the virtual representation of the patient's upper and/or lower ridges (112, 112). Where the virtual teeth set (113) is preconfigured in a fixed position corresponding to the shape of an arch, all of the teeth (117) of both the upper and lower portions of the virtual denture teeth design (113) move in unison, and rotation of the virtual denture teeth design does not result in independent movement or rotation of individual virtual teeth (113).

In one embodiment, where the pre-designed virtual denture teeth set comprises a pre-designed virtual gingival boundary line (FIG. 3, at 35), a set of computer executable instructs is applied to automatically create a gingiva that extends between the virtual denture teeth design and the 3D representation of the patient. Population of a gingiva that extends from the virtual denture design to the 3D representation of the patient may be performed in one step. A set of executable instructions from a software program may be used, for example, to modify virtual outer and inner gingival surfaces, and/or to add root eminence by the use of a mouse through a user interface. The virtual denture may further comprise a virtual base region that is adapted to conform to the 3D representation of the patient's palate and edentulous ridge. The virtual base region may comprise virtual hard and soft palate regions and/or a region designed to correspond to the maxillae and/or mandible of the patient.

Information relating to the virtual denture may be recorded. A digital data file of the virtual denture may be created and stored, for example, on a memory device of the computer system, which can then be accessible to the automated manufacturing system by a network interface. In one embodiment, the digital data file of the virtual denture may be transferred to a separate computer system and software program suitable for use in an automated manufacturing process.

In one embodiment, a non-transitory computer readable medium is provided having one or more computer instructions stored thereon, wherein the computer instructions comprise instructions for carrying out a method of designing a virtual denture by transferring at least a portion of a digital representation of patient scan data to the virtual denture teeth design. The methods described may be implemented via software run on a computing or processing system executing the computer instructions. The computer instructions may be provided by a program code or codes located, for example, on a computer memory, or accessible through a computer network, such as a local network. Thus, a method is described comprising a computer implemented method of designing a virtual denture comprising selecting a virtual denture teeth design from a plurality of designs, wherein the virtual denture teeth design comprises a teeth set that is prearranged in a fixed position in an occlusal scheme corresponding to an arch shape and size; virtually applying the design to a virtual 3D representation of a patient's oral anatomy; virtually aligning the design and the virtual 3D representation of the patient's oral anatomy; and virtually applying a virtual gingival boundary line of the virtual denture teeth design to form a virtual gingiva between the virtual denture teeth design and the 3D representation of the patient's oral anatomy to generate a virtual denture.

Automated Manufacturing Processes

Advantageously automated systems (508) may be used to form a physical model of a denture device from a virtual denture. The resulting physical model may have detailed characteristics of the patient's oral anatomy, as obtained from the digital data. Additive manufacturing processes, such as 3D printing, can quickly form a physical model from a virtual denture. Subtractive manufacturing processes, such as milling may also be used to form the physical model from the virtual denture. Gingival features and palatal contours unique to the patient may be faithfully replicated from the virtual denture. A physical model of a virtual denture formed with the patient's unique characteristics have a custom fit since the characteristic features of the soft tissue are important to providing a secure fit.

FIG. 12 illustrates a physical model (120) of a virtual denture having upper and lower portions that fit on the upper and lower edentulous ridges of a patient, constructed by the methods described herein. In one embodiment, the physical model is a 3D printed denture (120) having printed features replicating the virtual denture features of the upper and lower virtual arches, anterior and posterior teeth regions, and surrounding gingival regions. In one embodiment, the 3D printed denture comprises a printed upper portion (121) having a printed base that fits securely to the palate and maxillae of a patient, and a printed lower portion (122) having a printed base that fits securely onto the mandible of the patient. The physical model further comprises printed anterior (124) and posterior (125) regions, corresponding to the printed anterior and posterior teeth regions and printed anterior and posterior gingival regions. Additionally, the physical model comprises inner (126) and outer (127) gingival regions, a ridge region (128) between teeth regions and gingival regions, and a printed palate region (129).

In one embodiment, the automated manufacturing process is a 3D printing process, and a 3D printer may be connected directly to a computer system (500) used to design the virtual denture, or it may be connected to a remote computer by a network interface (510) that receives a data file for the virtual denture. 3D printing systems capable of converting the virtual denture to a physical model are suitable for use herein. Suitable printing devices include but are not limited to printers based on masking technology, continuous jet stream printers and drop-on demand stream printers. For example, both a raster and vector type apparatus can be used. A raster apparatus may comprise multiple print heads that moves back and forth across a layer. A vector apparatus may use one nozzle to draw the entire cross-section. Examples of suitable 3D printing devices include 3D printers manufactured by 3D Systems (Valencia, Calif.) and Stratasys (Minneapolis, Minn.)

In one embodiment, an automated manufacturing system (508) comprises a 3D printing system which can be used with the methods described. The 3D printing system may comprise a computing device, a 3D printer having a printer controller and a 3D print head module. The 3D printer can be any suitable 3D printing machine that is capable of forming a 3D physical model of the virtual denture that is suitable for use as a functional fitting replica denture. The 3D printer may include a buffer memory for receiving a print file in the form of signals from the computing device, an image buffer for storing printing data, and a printer controller that controls the overall operation of the 3D printer. The printer controller may control, for example, one or more printer drivers for driving the 3D print head module and associated transport mechanisms. A data store (local memory) and a display unit for setting the parameters of the printer may also be included.

Suitable computing systems may include personal computers such as those having Pentium IV microprocessors supplied by Intel Corp. USA with memory and graphical interface such as Windows 98, 2000, ME, XP (Microsoft Corp. USA). A computing system may include a microprocessor and associated memory for storing or buffering source images, intermediate arrays of data and calculations as well as the print files. Examples include volatile random access memory (RAM), non-volatile read/write memory such as a hard disc as well as non-volatile read only memory (ROM).

A computer program software product providing a printing method for printing the 3D representation of the virtual denture is executed on the computing device. In one embodiment, the computer program may be stored on a data carrier such as a CD-ROM or diskette, storing the computer program in a machine readable form that is capable of executing a printing method. In another embodiment, a computer program software product may be provided via the internet or a company intranet for download to the computing device transmitting the computer program software product over a local or wide area network.

Various materials may be used for forming the 3D physical model of the virtual denture. Polymeric materials suitable for use herein include but are not limited to polyamides, polyesters, polyolefins, polyimides, polyacrylates, polyurethanes, vinyl esters, or epoxy-based materials. Other polymeric materials include styrenes, styrene acrylonitriles, acrylonitrile butadiene styrene (ABS) polymers, polysulfones, polyacetals, polycarbonates, polyphenylene sulfides and the like. In one embodiment, polymeric materials include those based on acrylic and methacrylic monomers. In another embodiment, polymers suitable for use herein include but are not limited to acrylonitrile butadiene styrene (ABS), polycarbonate (PC), polylactic acid (PLA), high density polyethylene (HDPE), PC/ABS, and polyphenylsulfone (PPSU).

The physical model of the virtual denture (120) is constructed to fit securely into the mouth of the patient with little or no finishing. Where the physical model is printed to correspond with the virtual denture that has been designed with patient-specific data, it conforms to the contours of a patient's oral anatomy and fits securely on the patient's edentulous ridge.

Forming a Mold of the Physical Model

After formation of a physical model by an automated manufacturing process, the physical model may be modified by adding actual denture teeth to form the functional fitting replica denture. In one embodiment, a method comprises an automated process of setting denture teeth, and forming a gingival architecture that replicates the virtual denture design. In this process, inconsistencies and inaccuracy that occur through known manual, or 'by-hand', waxing and setting processes can be avoided.

To provide a location in which to incorporate actual denture teeth in the physical model, at least a portion of the material of the physical model may be removed. In one embodiment, substantially all of the material that corresponds to the anterior and posterior teeth regions of the physical model is removed. In another embodiment, only a portion of the teeth regions of the physical model is removed. In a further embodiment, a gap is formed in a portion of the physical model to provide a space for the denture teeth.

To ensure that the placement of the actual denture teeth replicates the orientation and occlusal scheme of the virtual denture and the physical model, in one embodiment, a mold of the physical model is formed prior to removing material from the physical model. The mold replicates details of the region of the physical model in which the denture teeth will be located. Thus, in one embodiment the mold captures the exact position, size, occlusal scheme, and alignment of the teeth as prescribed by the virtual denture design. Further, the mold may provide a guide for positioning actual denture teeth on the physical model by automatically recreating the teeth position and occlusal scheme. Moreover, the mold may replicate the gingival architecture that has been created in the physical model. By gingival architecture, it is meant the soft tissue characteristics, features and details of the inner and outer gingival regions, anterior and posterior gingival regions, and/or palate regions of the patient that have been provided by the patient data and replicated in the virtual denture and physical model. The gingival architecture can be formed in the functional fitting replica denture by use of the mold, in a reproducible manner according to the virtual denture design. The mold may be made by any known processes for making molds or impressions in dental restoration, and the mold may be made of the entire physical model of the denture or a portion of the physical model. The mold may be formed from stone, alginate, silicone, rubber, and the like.

In one embodiment, with reference to FIGS. 13a and 13b, a mold is made of the anterior teeth region, a portion of the posterior teeth regions, and the surrounding gingival regions of an upper portion of a physical model (131) and a lower portion of a physical model (131') by pressing a formable material (130, 130') on the regions. A mold may be taken of the entire teeth region of the printed model, or only a portion of the anterior and posterior teeth regions. FIGS. 13a and 13b, illustrate an example of a mold wherein the second molars (132, 132') are not incorporated into the mold. In a further embodiment, a moldable material is pressed onto the palate of a physical model. When sufficiently hardened to remove without compromising the impressed details, the hardened moldable material is removed to form a mold. A method for making the mold of the anterior region of the 3D printed denture includes applying a moldable material on a portion of the 3D printed physical model that corresponds to anterior teeth region corresponding to cuspids, central incisors and lateral incisors, and gingival structures surrounding the anterior teeth. In another embodiment, the formable material is applied to anterior and posterior teeth regions corresponding to the central incisors, lateral incisors, cuspids (canines), first bicuspid (first premolar), and second bicuspid (second premolar), and a portion of the gingival regions surrounding the teeth incorporated in the mold. In a further embodiment, a mold may be formed that further comprises an impression of the first molar and optionally, the second molar, as well.

A mold comprises a relief of the characteristics and features the physical model of the virtual denture, such as the arch shape and size corresponding to the virtual denture. The mold further comprises recesses into which actual denture teeth are set, wherein the recesses have an orientation, size and shape corresponding to the virtual denture teeth, and the recesses are in the fixed prearranged position corresponding to the arch shape. The mold may further have an impression of at least a portion of the surrounding upper and or lower gingival regions, comprising gingival details and palatal characteristics present on the 3D printed denture.

Any method suitable for obtaining a dental impression, including for example, methods used to obtain an impression from a patient's oral anatomy in preparation of a restoration may be used to form the mold. Suitable materials for making the mold include sodium alginate, hydrocolloid, polyether and silicones including condensation cured silicones and addition-cured silicones, including polyvinyl siloxane (PVS).

Forming the Functional Fitting Replica Denture

At least a portion of the physical model may be removed for placement of the denture teeth. Any suitable technique for removing material may be used, such as a variable speed grinding hand-piece and bur, known for use in dental laboratories for finishing and/or detail work. Upon removal of the teeth region from the physical model, a ridge may be formed that bridges the inner and outer gingival regions.

Figure 14:
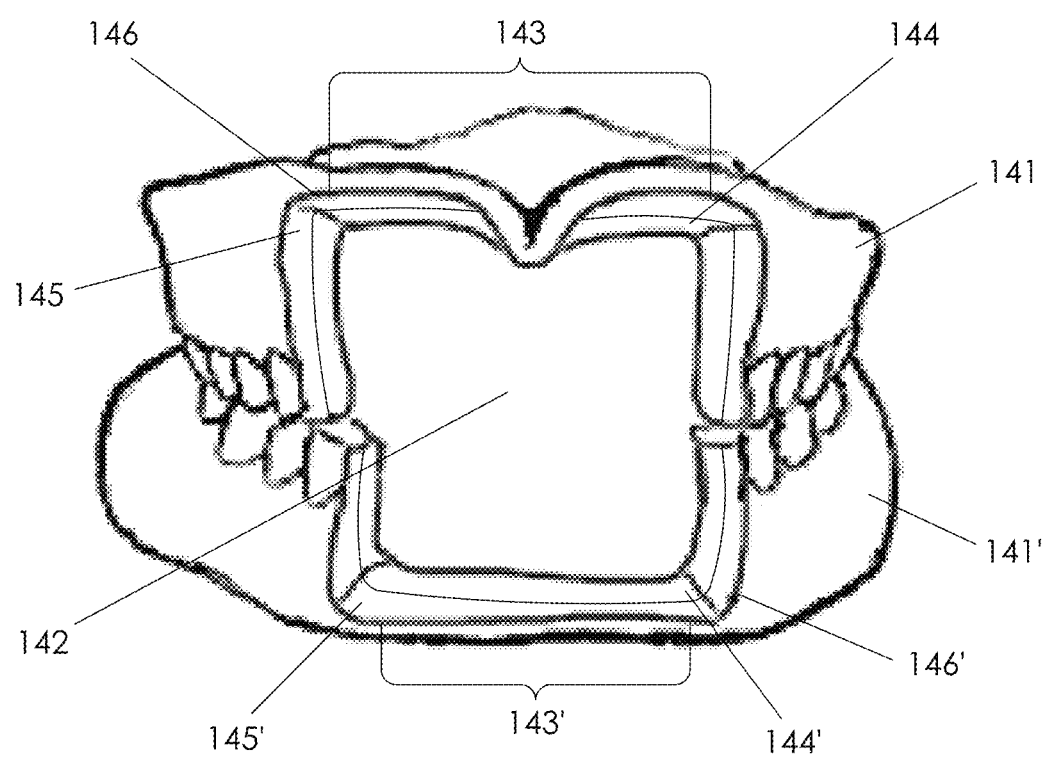
FIG. 14. A view of one embodiment of a physical model described herein.

In one embodiment, exemplified in FIG. 14, a portion of the physical model that corresponds to an anterior upper and/or lower teeth region (143, 143') and an upper and/or lower gingival region is removed, for example, by cutting out or grinding away the material. Upon removal of the anterior teeth region(s), an upper ridge (144) and/or a lower ridge (144') may be formed in the physical model. The ridges may bridge inner and outer gingival regions. In one embodiment, a ridge (144 and 144') is formed that is substantially parallel to the occlusal plane. The ridge may be substantially flat or planar, so that the ridge of the physical model (143) has no alveolar sockets or slots in which to set denture teeth. A sufficient amount of the physical model is removed to provide a distance between the ridge and occlusal plane enabling the actual denture teeth to be set in the gap (142) according to the design of the virtual denture, while maintaining the desired bite relationship.

In a further embodiment, an additional amount of the material of the physical model is removed corresponding to the anterior gingival region to form a gingiva indentation (145, 145') adjacent to the gap in the physical model. The gingiva indentation borders the gap and extends to a finish line (146, 146'). The gingiva indentation may be present in both the upper and lower gingival regions, and the gingiva indentation may border a part of the gap or it may border the entire gap The gingiva indentation provides an area within which to replicate the patient's gingival architecture in a formable material according to the virtual denture while maintaining the dimensions of the printed physical model.

All or a portion of actual denture teeth that correspond with the virtual teeth set of the virtual denture design may be obtained for placement on the physical model. Denture teeth may comprise an acrylic material, or any other material suitable for use as denture teeth. The mold (130) of the physical model may serve as a guide for positioning denture teeth in relation to the physical model. In one embodiment, to incorporate the denture teeth into the physical model, the mold having teeth set in the mold recesses and the physical model may be assembled, positioning the denture teeth, for example, in a gap (142). Formable material may be introduced into the mold to set the teeth in place in the gap. In one embodiment, the mold is injected and filled with a formable material, e.g., through injection channels in the mold. A portion of each of the denture teeth may be embedded in the formable material to hold them in place in the gap. The mold and the physical model may be disassembled after the formable material is hardened, revealing the functional fitting replica denture.

Figure 15:
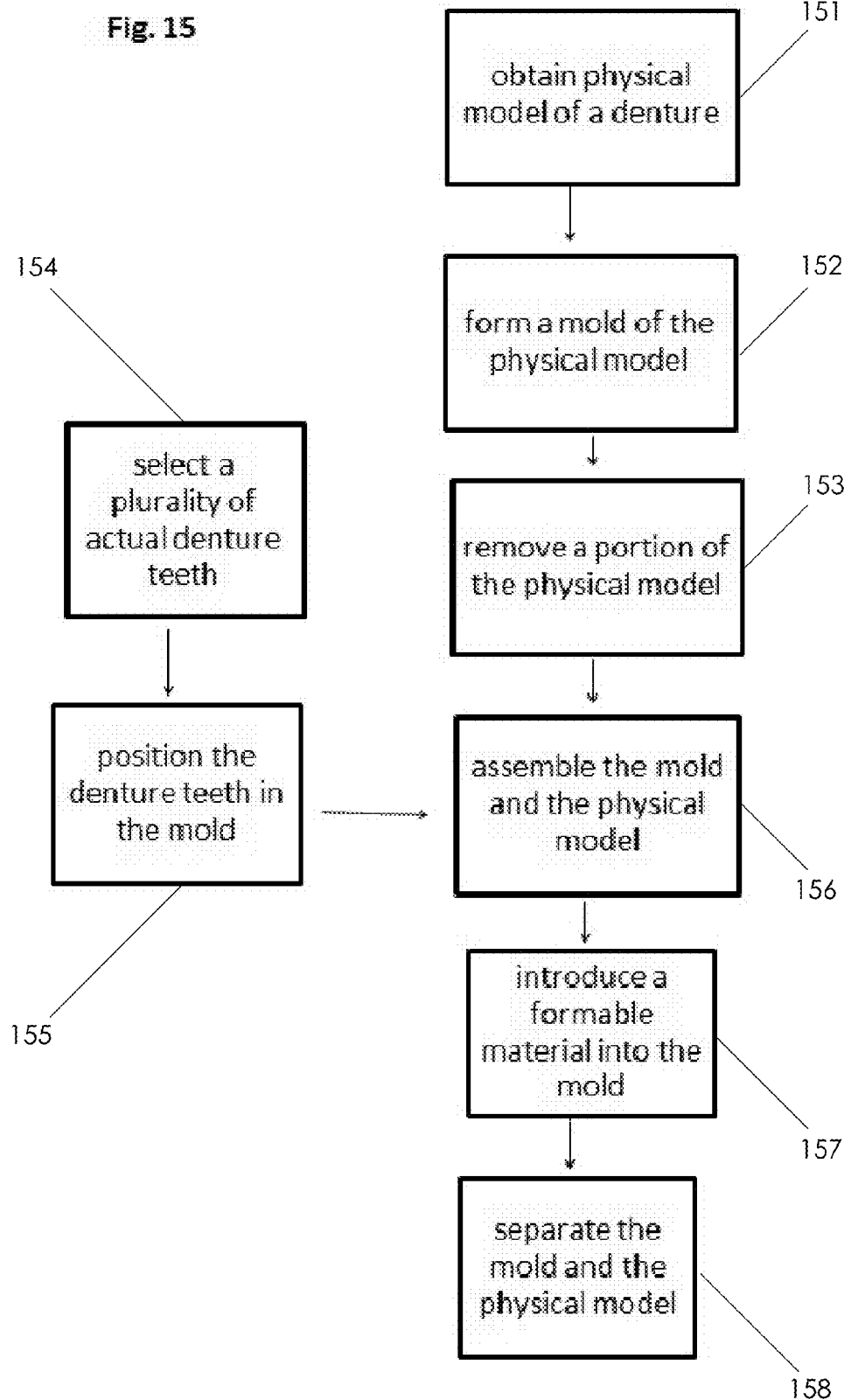
FIG. 15. A diagram of a process described herein.

Thus, in one embodiment, a method for making a functional fitting replica denture is described comprising the following steps as outlined in FIG. 15: obtaining a physical model of a denture (151), optionally made by a rapid manufacturing process; forming a mold of at least a portion of the physical model (152); removing a portion of a physical model (for example, that corresponds to an anterior teeth region) to form a gap and a ridge (153); selecting a plurality of actual denture teeth (154); positioning the denture teeth in the mold (155); assembling the mold and the physical model (156), using a mold of the physical model to form a guide for placement of denture teeth in position in the gap of the physical model; and introducing a formable material in the mold (157), to hold the actual denture teeth in position in the gap of the physical model, adjacent the ridge; and separating the mold and the physical model (158), creating a functional fitting replica denture.

Figure 2:
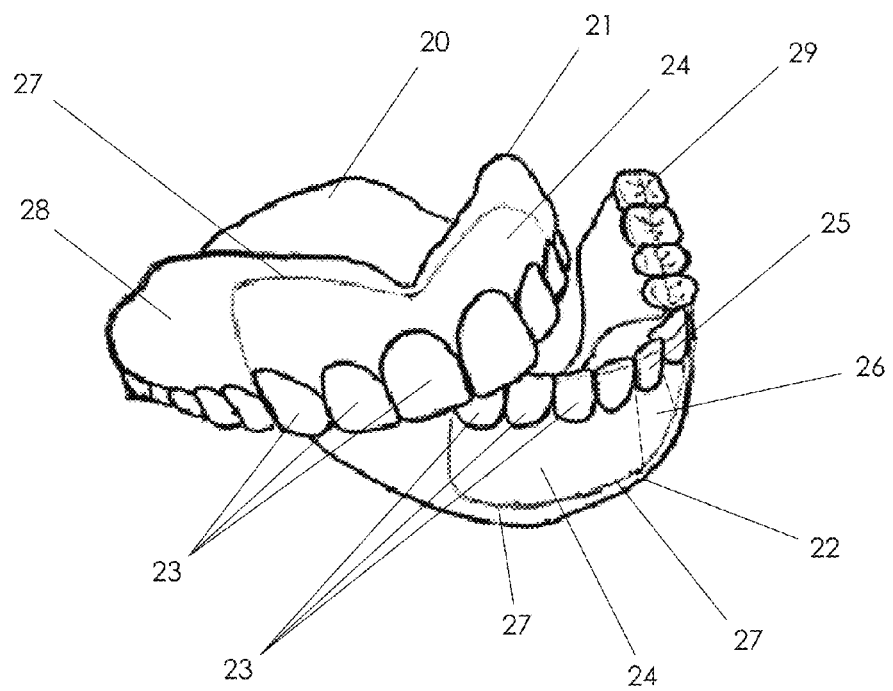
FIG. 2. A functional fitting replica denture according to an embodiment described herein.

A functional fitting replica denture, as illustrated in FIG. 2, comprises an upper part (21) and a lower part (22), each having a base (20) with an inner shape that fits securely on the maxillae and mandible of an edentulous patient. Actual denture teeth (23), shown with teeth details (29) on the occlusal surface, are embedded in formable material (24) that fills the gap (FIG. 14, at 142) of the physical model (28). In one embodiment, a portion of the denture teeth corresponding to the crown (25) is exposed, (i.e., not embedded in the formable material), and a portion corresponding to a neck (26) of the tooth may be embedded in the formable material. The formable material (24) fills the gap and abuts the ridge of the gap. The denture teeth may be adjacent the ridge of the physical model and may be held in place by the formable material.

In a further embodiment, a functional fitting replica denture is formed that comprises a first portion comprising a physical model of a denture that fits securely in the mouth of a patient that comprises a first material. The first portion comprises first and second posterior teeth regions, a gap between the posterior teeth regions that corresponds to an anterior teeth region; an anterior gingival region adjacent the gap; and a ridge between the posterior teeth regions adjacent an anterior gingival region. The functional fitting replica denture further comprises a second portion, comprising a second material, discrete from the physical model of the denture, that at least partially fills the gap and holds a plurality of denture teeth (23) in position. In one embodiment, the ridge is substantially flat, and the denture teeth are adjacent the flat ridge. In one embodiment, a functional fitting replica denture is formed wherein the denture teeth positioned in the gap of the physical model of the denture are anterior denture teeth; in one embodiment the denture teeth comprise six of the upper anterior most teeth, including the central incisors, lateral incisors, and cuspids. In a further embodiment, a functional fitting replica denture is formed wherein the denture teeth positioned in the gap of the physical model of the denture comprise six upper teeth and six lower teeth, including four central incisors, four lateral incisors and four cuspids.

In one embodiment comprising a gingiva indentation in the gingival regions of the physical model, formable material (24) fills the gingiva indentation, and tapers to the finish line (27) of the physical model providing a gingival architecture comprising the formable material. The portion of the gingival architecture constructed from the formable material does not add to the thickness of the physical model. Thus, maintaining the dimensions and proportions of the patient's gingival architecture. The gingival architecture replicates the patient's oral anatomy that was incorporated into the virtual denture design. The gingival architecture made from the formable material has a size and structure corresponding to the patient's information, and therefore conforms to the patient's oral anatomy providing a precise patient-specific fit. Where the process for making the gingival architecture is automated by use of a mold, and incorporates patient data, the process is standardized when compared to traditional wax-up process, making the gingival architecture consistently reproducible. Thus, whereas traditional manual waxing does not replicate the patient's specific fit and characteristics, the automated process creates a gingival architecture made from formable material that replicates the patient's gingival structures.

Formable materials suitable for use herein include, for example, flowable composite materials, hydroplastic materials, and thermoplastic materials. In one embodiment, the formable material is a wax. Formable material may be material that can be softened again, for example, by heat, after hardening. In one embodiment, where it is determined that a modification of the position of the teeth or of gingival region is required or desired, the formable material may be softened for re-positioning of the denture teeth. The formable material is introduced into the cavity by any known techniques, for example, by injection molding a formable material by machine or syringe.

In one embodiment, the functional fitting replica denture comprises a first material comprising the printed material, a second material comprising the formable material such as a wax, and a third material that is used for making the denture teeth that is different from the first and second material. The first material may be a substantially rigid, that will not deform when inserted into the mouth of a patient for evaluation. The second material holds the denture teeth in place, and is a formable or substantially formable material, including thermoformable materials and thermoplastic materials such as wax. The formable material may allow the teeth to be set in place for try-in and bereadily movable by a dentist or laboratory technician.

Where the functional fitting replica denture comprises both a first portion corresponding to the physical model and a second portion corresponding to the formable material made from the mold, and where both incorporate information of the patient's oral anatomy, the functional fitting replica denture fits securely in the mouth of the patient. The functional fitting replica denture and any modifications to the functional fitting replica denture may be scanned, recorded and stored, for example, as digital files, that can be reproduced. Moreover, the virtual denture files may be modified based on any modifications to the functional fitting replica denture after evaluation by the patient and dentist. The modified virtual denture files may be recorded, saved as a digital file, and stored. In one embodiment, upon loss or destruction of the final denture, the digital file of the virtual denture may be retrieved and a new physical model of the denture can be created, for example by an automated manufacturing process.

In a further embodiment, a method is described for making a partial denture for a partially edentulous patient that comprises method steps that were used in making a full denture. A partially edentulous patient has at least one edentulous ridge region for which a partial denture restoration is desired. Digital data of the patient's oral anatomy is obtained that comprises information about the edentulous ridge region(s) and surrounding teeth and/or gingiva regions. The digital data file may be converted into a 3D representation of the patient's oral anatomy, in a format that is compatible with a dental software restoration program for designing a virtual partial denture. Virtual denture teeth designs may be created that are suitable for use in partial dental restorations, and may be stored, for example, on a local or remote memory. In one embodiment, a plurality of virtual denture teeth designs may be created that are suitable for a multiplicity or a majority of patients in need of a partial denture restoration. The virtual partial denture may be prepared by known software programs that apply and align a patient's digital data information with a digital virtual denture design, in a manner described above, for the virtual denture. Patient data may be transferred via execution of design software instructions to the virtual denture teeth design, to incorporate patient specific data regarding existing dentition, gingiva and palatal characteristics, bite relationship data, and the like, to form the virtual partial denture.

In another embodiment, dental design software programs may be used to modify a digital data file of a partially edentulous patient by incorporating virtual teeth that are provided as part of a remote or local library, as described above. A digital file of the virtual partial denture may be provided in a format compatible with an automated manufacturing system, such as those described herein (for example, a 3D printing process). In one embodiment, after formation of a virtual partial denture, a partial physical model may be made, for example, by an additive manufacturing process, or a subtractive process. In one embodiment, a mold is formed of at least a portion of the physical partial denture model that corresponds to one or more edentulous ridge regions where replacement or denture teeth will be located, for example, one or more teeth from the posterior or anterior teeth regions. In a further embodiment, the mold is formed of the ridge regions where replacement or denture teeth will be located, and, still further, the mold may include impressions of additional teeth or gingiva on each side of the tooth or teeth to be replaced. After formation of a mold according to processes described herein, one or more portions of the physical model may be removed to form a gap, a ridge, a gingiva indentation of the gingival regions, and/or a finish line, in a region or regions that correspond to the location of replacement or denture teeth. Denture teeth may be set in the mold which is used to guide the teeth into position adjacent the ridge of the gingival region. A formable material is introduced into the mold to set the denture teeth in place in the physical model of the partial denture in a position corresponding to the virtual partial denture, for example, by injection the formable material. Upon completion and evaluation of the functional fitting replica denture, a final partial denture may be formed using processes described herein, or those known in the art for processing dentures and partial dentures.

In a further embodiment, it may be desirable to wear a denture design for an extended or long term trial period prior to forming a final denture. Thus, in one embodiment, the physical model of the denture may be worn prior to forming a functional fitting replica denture, or instead of forming the functional fitting replica denture. In this manner, the patient may have an extended opportunity to wear the physical model to check for bite relationship while biting and chewing, and/or to allow the patient an extended opportunity to check the appearance of the physical model outside of the dentist's office. In one embodiment, a portion of the thickness of the gingival region of the physical model is reduced, while leaving the teeth regions of the physical model intact. In one embodiment, a portion of the physical model that corresponds with the anterior gingival region is reduced by grinding with a handpiece, thereby providing an anterior gingival indentation surrounding the anterior teeth regions (for example, teeth regions corresponding to the central and lateral incisors, and cuspids). Formable material, such as a colored wax (e.g. a color matching the patient's actual gingiva), may be introduced in the gingival indentation to provide a patient with a realistic appearance of the final denture. The formable may be introduced into the gingival indentation by hand. Alternatively, formable material may be introduced via a mold of the gingival region as described above. In one embodiment, a method comprises obtaining a physical model of a virtual denture of a patient, obtaining a mold of a gingival region of the physical model, removing a portion of the gingival region surrounding the teeth, assembling the mold and the physical model, and introducing a formable material into the mold to form a physical model comprising a gingival architecture comprising formable material that replicates the patient information. Because a large portion of the physical model remains intact, the resulting modified physical model may be suitable for a long term use.

Device for Determining the Vertical Dimension of Occlusion

To evaluate proper position of the teeth and to determine the positional relationship between upper and lower denture teeth, a device to register the bite of a patient may be used. In one embodiment, exemplified in FIG. 4, an apparatus for determining the vertical dimension of occlusion (40) is provided that comprises an upper functional fitting replica denture (41) formed by the processes described herein, and a lower occlusal recording device (42). They may be used together by insertion into a patient's mouth, for purposes of evaluating and determining the vertical dimensions of occlusion in an edentulous patient by a dentist. Because the upper functional fitting replica denture (40) comprises a base (43) portion having an inner shape that fits securely to the patient's palate and maxillae, an accurate bite relationship may be established by a dentist, increasing the accuracy of the fit, providing a better bite, and reducing likelihood that the final denture will be returned to the dental lab for adjustments. Advantageously, the number of visits required by the patient can be reduced wherein both the evaluation of the functional fitting replica denture and evaluation of bite relationship may occur in the same visit. Traditionally, evaluation of a try-in denture was conducted in a first visit, followed by a second visit for evaluation of bite registration.

In one embodiment, an apparatus for determining the vertical dimension of occlusion in an edentulous patient comprises 1) an upper functional fitting replica denture comprising a physical model made from an automated manufacturing process and anterior denture teeth embedded in a formable material that substantially fills a gap in the physical model, and 2) a lower deformable occlusal recording device. In one embodiment, an apparatus (40) for determining the vertical dimension of occlusion comprises a first part that comprises an upper functional fitting replica denture (41) as described herein, that fits securely on the maxillae of the patient. The first part comprises a first material portion (44) having a gap that corresponds to at least a portion of an anterior teeth region and a ridge adjacent an anterior gingival region. The first part of the apparatus further comprises a second material (47), different and/or discrete from the first material, at least partially filling the gap in the first portion and abutting the ridge (48; not readily observable through the second material, as depicted by the dashed line), and extending to the finish line (46); and a plurality of anterior denture teeth (45), each tooth comprises a portion that is embedded in the second material. The second part of the apparatus comprises a lower occlusal recording device (42) comprising a deformable material, such as a wax, dental rubber, or silicone. Data obtained from the occlusal recording device may be scanned and recorded, and used in the process of forming a denture device.

Processing a Final Denture

The final denture comprising the actual denture teeth may be made by any method known in the art for processing a final denture from a functional fitting replica denture. For example, an impression is taken of the functional fitting replica denture by setting it into an impression material, such as hydrocolloid. Upon solidification of the colloidal, the formable material of the functional fitting replica denture may be removed, for example, by melting the material and pouring it out, leaving denture teeth in the designed position within the impression. The physical model portion of the functional fitting replica denture is also removed, and any additional actual denture teeth needed for the final denture, that correspond to the virtual denture, are placed within recesses left by the physical model portion of the functional fitting replica denture. A material suitable for forming the gingival portion of a denture, such as acrylic, is poured, and a final denture having actual denture teeth is formed.

The processes for making the final denture according to methods described herein advantageously reduce processing time over traditional denture processes. The final dentures produced by these methods substantially conform to the oral anatomy of the patient. While polishing may be desired, removal or addition of significant material may not be necessary since the final denture corresponds to the appropriate thickness of the virtual denture, the physical model and the functional fitting replica denture. In contrast, traditional denture-making processes frequently require the addition or elimination of denture material to achieve uniform thickness and a fit that corresponds to the patient's oral anatomy, as well as trimming, grinding and polishing. Where traditional processes result in removing material to obtain a uniform thickness, loss of features such as root eminence results; therefore, additional finishing may be required to reincorporate features lost in the grinding process of traditional denture processes. The methods described herein advantageously reduce these limitations.

Figure 16:
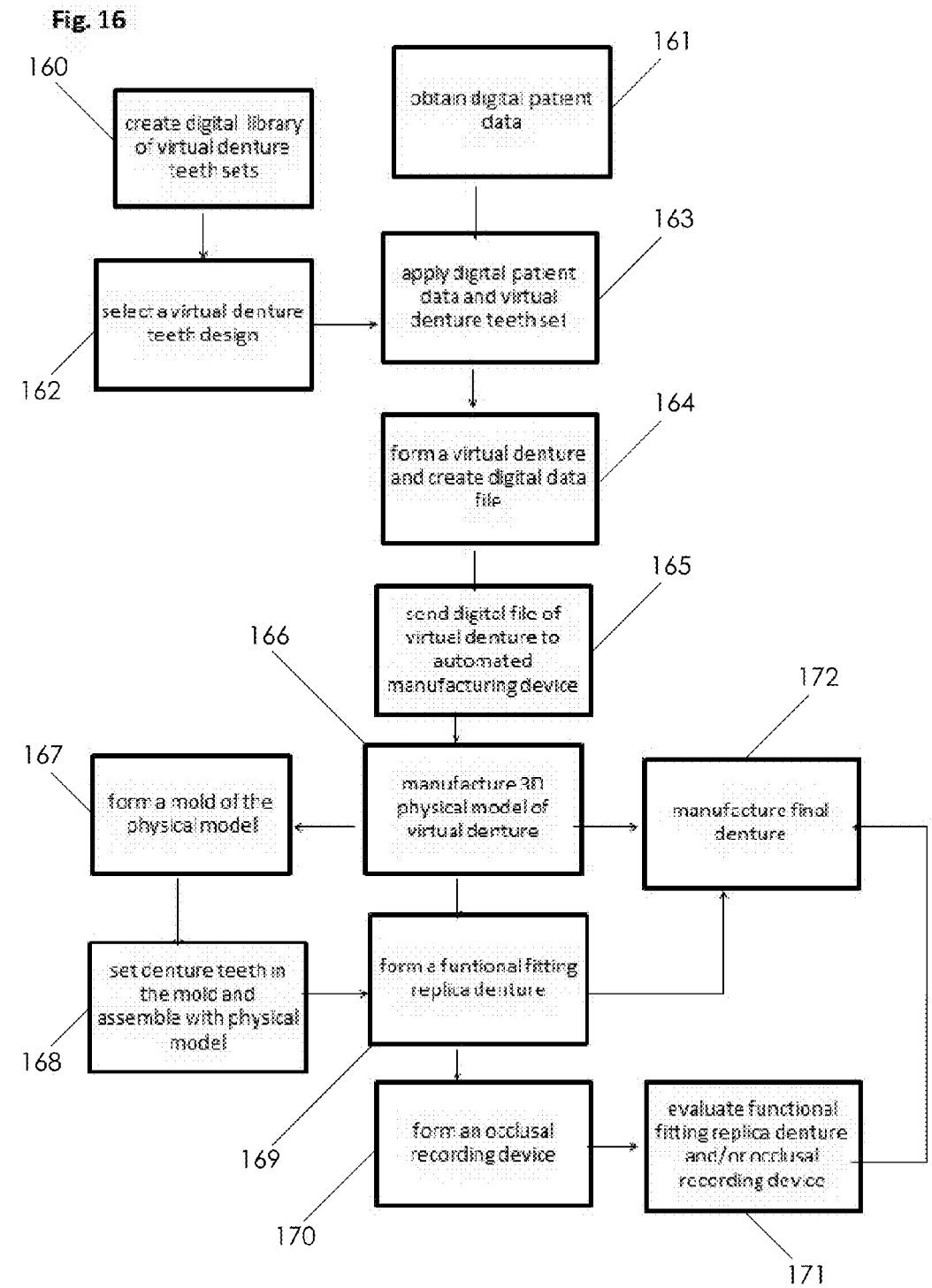
FIG. 16. A diagram of a process described herein.

With reference to FIG. 16, a method of making a denture device is provided that comprises the steps of: creating a digital library of virtual denture teeth designs (160); obtaining a virtual three-dimensional (3D) representation of a patient's oral anatomy (161); selecting a virtual denture teeth design (162) having a virtual teeth set prearranged in a fixed position in an occlusal scheme corresponding to a specific arch shape; applying the virtual dental teeth design to the virtual three-dimensional representation of the patient's oral anatomy (163); aligning the virtual denture teeth design and the virtual three-dimensional representation to generate a virtual denture (164); sending the digital data file of the virtual denture to an automated manufacturing system (165); and manufacturing a 3D physical model of the virtual denture (166). In one embodiment, the final denture may be produced directly from the physical model of the virtual denture (172). In a further embodiment, a functional fitting replica denture may be formed (169) prior to manufacturing the final denture (172) by forming a mold of the physical model (167) and modifying the physical model by removing a portion of it to incorporate actual denture teeth (168) in the mold, assemble the mold and physical model, and introduce a material to set the teeth in place, to form the functional fitting replica denture (169). The method may further comprise forming an occlusal device (170) from the functional fitting replica denture and a deformable lower portion, which can be used for evaluation (171) prior to processing the final denture (172).

Method steps recited may be performed in any order in order to arrive at a denture device; thus, no particular order is implied or required where the ordering of steps is unnecessary to arrive at a particular device. The final denture has high precision with regard to fit and orientation advantageously reducing the likelihood that the denture will be returned by a patient for improper fit. Moreover, because the final denture is formed from an impression of, for example, a 3D printed denture, the final denture requires less material to be removed and fewer modifications. Processing of a final denture made according to the methods described herein require only slight modifications such as smoothing surfaces.

EXAMPLES

Example 1

A plurality of virtual denture teeth designs were formed, each design having a teeth set prearranged in a fixed position in an orientation corresponding to a fixed arch shape, and having a virtual gingival boundary line.

A plurality of wax denture set-ups was prepared as follows. Data from multiple patients were obtained for arch shape, bite relationship, teeth alignment and orientation. Additionally, patient measurement data were obtained for molar-to-molar distance (i.e., the distance between second molars) of the mandible and maxillae, as well as canine-to-canine distance; both distances were measured straight across the arch. Measuring from the front of the arch to the back of the arch, the distance between incisive papilla and the center point between the second molars was obtained. Further, the vertical dimension of occlusion of the mandible and maxillae was obtained from patient data. The data were obtained from patient records, stone models, and/or final dentures that were previously prepared by traditional denture manufacturing techniques. From an analysis of the data, a multiplicity of designs were created to accommodate the measurements, arch shapes, and teeth alignments of a majority of patients. Designs were created having several arch shapes, including square, tapering, and ovoid. The designs were also specific to teeth size, such as teeth widths and lengths to accommodate a variety of arch sizes, variations in vertical dimensions of occlusions, and preferences in teeth shape, such as square, ovoid or tapering. The designs were created having teeth set in specific alignment around an arch, such as an ideal alignment, feminine alignment, or masculine alignment. Further, designs were created for lingualized and cross-bite occlusion, in several arch sizes.

Each design comprised an upper and lower portion, corresponding to an upper and lower arch. Each design was prepared as a wax set-up, creating a plurality of wax set-ups in various arch sizes and arch shapes. Wax set-ups were formed by shaping wax into a particular arch shape to form a wax rim. Actual denture teeth (Kenson® denture teeth) of appropriate size and shape to correspond with a particular design were positioned around a wax rim. Wax rims corresponding to upper wax set-ups were further adjusted by aligning teeth in ideal, masculine or feminine arrangements. The lower portion of the wax set-ups was prepared in ideal arrangements.

When finished, an impression was taken of each wax set-up, and stone models were formed of the upper and lower portions for each design. The impressions and stone models were prepared by standard denture making techniques for forming impressions and stone models. The stone models comprising an upper and lower portion were scanned using a 3Shape desktop scanner to create a digital data file for each design in .dcm format. The digital data file was exported into an .stl file to create a virtual 3D representation of each stone model for use with 3Shape software.

Using design software programs, instructions were executed on a computer system to design a plurality of virtual denture teeth designs from the virtual 3D representation of the stone models. The virtual stone models were trimmed using software cutting tools to remove substantially all features of the stone model, such as the base, leaving the virtual teeth sets. User interfaces provided for design control via a display unit wherein standard tools provided by dental design software operated by executable instructions, such as those seen in the screen shot of FIG. 11, were available to form the virtual denture teeth designs. A virtual gingival line was created on the upper and lower teeth sets of each virtual denture design. Using the design software, points were applied, for example, in multiple locations on the buccal and lingual surfaces of each tooth of the virtual teeth sets, as well as points corresponding to the interproximal regions. Using design software, the points were joined with an intersecting line to form a virtual gingival boundary that traversed adjacent teeth, across the entire teeth set to connect adjacent teeth. The teeth of the virtual denture teeth designs correspond to the teeth used in the wax set-ups which were Kenson® denture teeth (Myerson, LLC.).

A plurality of virtual denture teeth designs were formed in this manner. The resulting virtual denture teeth designs were saved to a memory of a computing system, examples of which are illustrated in Table 1. With reference to Table 1, measurements of the virtual denture teeth design were obtained. Molar-to-molar measurements represent the width measurements across an arch from the second molar to the second molar, measured in millimeters (mm). The incisive papilla distance represents the distance (mm) from the anterior of the design corresponding to the approximate location of where the incisive papilla will be located, to a posterior position that corresponds approximately to the center point between the second molars.

Virtual denture teeth design #1 (Table 1), is formed having virtual teeth set in a fixed ovoid arch shape. The teeth were oriented in a fixed position corresponding to a masculine arrangement of teeth. Virtual denture teeth designs 2-4 exemplify teeth sets that were arranged to accommodate an ovoid arch, and having teeth aligned in a feminine arrangement. Virtual designs numbers 2-4 exemplify designs having similar arch shape and teeth arrangements made in multiple sizes. For example, the vertical dimension of occlusion (VDO) differs in the designs even though the molar-to-molar distances are the same for designs 3 and 4. The differences between the designs accommodate patients, for example, having similarly sized arches when measured across the arch, but may require different sized teeth to accommodate variances in VDO. When comparing designs #2 and 3, design #3 accommodates a slightly longer overall arch length, however, both have the same measurement from anterior to posterior (incisive papilla distance).

Design numbers 5-7 described virtual denture teeth designs that also accommodate an ovoid arch. The teeth sets are aligned in a fixed position in an ideal orientation. Three sizes of the ovoid-ideal arrangement is shown. The design had variations in molar-to molar distance, and different anterior to posterior distances; the VDO is the same for designs 5 and 6, and smaller for design 7. Moreover, design details are set forth for some embodiments including tapering (#7) and square (#9) feminine arrangements, and lingualized (#10) and cross-bite (#11) arrangements.

Table 1 outlines examples of the virtual denture teeth designs. The measurements in Table 1 are specific to the upper portion of a denture teeth design corresponding to a maxillary arch design, and represent a full set of upper teeth. The examples in the table are not intended to be limiting, and designs having further variations in sizes were prepared for each arch shape and teeth alignment.

TABLE 1

Examples of Virtual Denture Teeth Designs.

| Virtual Denture Teeth Design # | Orientation-Arch Shape | Teeth Arrangement | Molar-to-Molar Distance* (mm) | Incisive Papilla Distance** (mm) | VDO*** (mm) |
| --- | --- | --- | --- | --- | --- |
| 1 | ovoid | Masculine | 49 | 40 | 19 |
| 2 | ovoid | Feminine | 49 | 40 | 19 |
| 3 | ovoid | Feminine | 50 | 40 | 20 |
| 4 | ovoid | Feminine | 50 | 44 | 22 |
| 5 | ovoid | Ideal | 48 | 41 | 22 |
| 6 | ovoid | Ideal | 50 | 40 | 22 |
| 7 | ovoid | Ideal | 53 | 42 | 20 |
| 8 | tapering | Feminine | 47 | 44 | 21 |
| 9 | square | Feminine | 49 | 34 | 22 |
| 10 | lingualized | n/a | 55 | 42 | 20 |
| 11 | cross-bite | n/a | 53 | 44 | 21 |

*distance between second molars of upper arch in millimeters (mm).
**distance between incisive papilla and center point between molars in mm.
***VDO—vertical dimension of occlusion measured in mm.

Each virtual denture teeth design comprises both an upper part, corresponding to a virtual teeth set for an upper arch, and a lower part corresponding to a virtual teeth set for the lower arch. The resulting virtual teeth designs were saves as digital data files that may be located within a design library stored locally or remotely, and accessible via network interface.

Example 2

A functional fitting replica denture according to one embodiment was designed as described herein.

Impressions of an edentulous patient's maxillae and mandible were taken at a dentist's office and a stone model was formed. The stone model was scanned with a desk top scanner and data was uploaded to software program for forming a virtual denture (3Shape desk top scanner and Dental Designer™ software program).

Measurements from the digital image of the scanned stone model were taken as follows. Tuberosity-to-tuberosity distance was measured to be approximately 46 mm, when measure across the width of the upper arch. The tuberosity distance corresponds approximately to the distance between right and left second molars of the upper arch, as measured directly across the width of the arch impression. The retromolar pad-to-retromolar pad distance was measured to be approximately 49 mm, when measured across the width of the lower arch. The retromolar pad distance corresponds approximately to distance between the locations of second molars on the lower arch, as measured directly across the width of the arch impression. The vertical dimension of occlusion was measured to be about 24 mm. Distance between the incisive papilla in the anterior of the mouth, and a posterior point mid-way between the right and left tuberosity locations when measured across the width of the arch, was measured to be about 40 mm. The upper and lower portions of the digital image of the scanned stone model were marked for location of a gingival region using customary software design tools.

A virtual denture was constructed on a computer system on to which dental restoration software was loaded, as follows. The shape of the patient's arch was determined to be ovoid, and the instructions from the dentist requested that the denture teeth be arranged in an ideal tooth arrangement. The patient data described above were used to select a pre-designed virtual denture teeth design from a plurality of designs from a design library that was stored on the computer. The stone model was observed to confirm the shape of the patient's ridge as an ovoid shape. VDO measurements and molar-to-molar distances were used to select a design having an appropriate size from among the predesigned virtual denture teeth designs of an ovoid shape having teeth in an ideal arrangement (i.e., design #5-7 in Table 1). A virtual denture teeth design #5 in Table 1, was selected based on arch shape (ovoid), teeth arrangement (ideal), and similarity in size to the features measured. The selected pre-designed virtual denture teeth design comprised a full set of teeth (upper and lower arches) that were prearranged in a fixed position having an orientation that corresponds to the ovoid arch shape. The pre-positioned teeth were aligned in an ideal arrangement, with the teeth being in a fixed position relative to each other The data file representing the virtual denture teeth design #5 was retrieved and aligned with a data file containing the scan data of the patient's stone model, in accordance with the dental design software program. Alignment of the virtual denture teeth design in relation to the patient's scanned arches was optimized using a computer mouse to make adjustments as seen on the display unit. The virtual denture teeth design was positioned in proper alignment with the scan of the patient's arches by rotating and moving the design (left-right, up-down, and side-to-side) as a single unit, until the best alignment relative to the arches was achieved. Because the teeth were in a fixed position on a fixed arch shape, upon rotation of the design, none of the teeth of the teeth set moved separately from the unit. No modifications to individual teeth orientation or alignment, or arch shape and size were made.

The virtual denture teeth design had a preconfigured virtual gingival boundary line. After aligning the image of the patient data file with the image of the virtual denture teeth design, the virtual gingiva was automatically generated in a single step according to the preconfigured gingival boundary of the virtual denture teeth design and the virtual gingiva of the image of the patient's stone model. A virtual gingiva was generated that traversed adjacent teeth, and virtual interdental papillae were populated. Minor modifications to the gingival, such as adding additional gingival detail such as festooning was quickly accomplished with the aid of a computer mouse, in accordance with tools provided by the dental design software program. The resulting virtual gingiva corresponded to the virtual stone model and therefore characteristics of the patient's oral anatomy was transferred to the virtual design. The virtual base of the virtual stone model of the edentulous patient was cut away using available software tools, leaving the virtual gingiva and virtual denture teeth, and the virtual denture was completed. Data files corresponding to the upper teeth, lower teeth, upper gingiva and lower gingiva were stored in a memory device.

The upper gingival region data file and upper virtual teeth data file were merged; the lower gingival region data file and lower virtual teeth data file were merged by the computing system. Resulting virtual denture files were transmitted to a 3D printing system (3D Objet 500, by Stratasys), and using an acrylic-based polymer (VeroDent™ polymer, by Stratasys, Minneapolis, Minn.), were converted to printed upper and lower portions of a physical model of the virtual denture. The physical model corresponded to the size and shape of the patient's oral anatomy, having one portion fitting securely onto the upper ridge, and a separate second portion fitting securely onto the lower ridge, of the edentulous patient. The physical model comprised a 3D printed replica of the virtual denture, having the gingival architecture and soft tissue features of the patient which was replicated from the patient's stone model. The thickness of the physical model was approximately the same as the thickness of a final denture.

A mold of a portion of the 3D printed physical model was made corresponding to the cuspids (canines), lateral incisors, and central incisors, as well as a portion of the posterior teeth adjacent the anterior teeth (i.e., the first and/or second premolars), as follows. Mold material comprising a vinyl polysiloxane lab putty (Capture® Impression Materials, by Glidewell Direct) was pressed around the upper and lower anterior regions of the 3D printed physical model. The mold covered the teeth regions and surrounding gingival area above the teeth and well as a portion of the soft palate on the upper 3D printed portion. Upon hardening, the mold was removed and comprised recessions corresponding to the teeth and a replica of the surrounding gingiva of the physical model. The mold further comprised a relief that included gingival details and soft tissue characteristics unique to the gingival architecture of the patient.

A portion of the 3D printed physical model was removed with a handpiece for use in denture finishing and bur. On each of the printed upper and lower portions, the printed material was removed in teeth regions that corresponded to the upper and lower central incisors, lateral incisors and canines to form a gap. Additional printed material was removed corresponding to a portion of gingiva adjacent the printed teeth regions that were removed. By removing printed material, a flat, planar ridge was formed on each of the upper and lower printed portions in the region that corresponded to the gingival regions. Flat ridges bridged the inner and outer gingival areas of both the upper and lower printed portions. Because the ridge was substantially flat, the physical model lacked alveolar sockets; thus, no holes were formed to insert the actual denture teeth. Additionally, a planar indentation was formed around the gap on the upper and lower portions by removing material in the gingival regions adjacent to the gap, thus, forming the gingiva indentation. The gingiva indentation continued around the border of the gap and extended to a finish line. The gingiva indentation depth was less than the thickness of the physical model.

Denture teeth (Kenson® teeth, distributed by Myerson LLC) that corresponded to the virtual denture were inserted into the recesses of the mold. The mold and the physical model were assembled, with the denture teeth positioned in the gap of the physical model. Wax was injected through an injection channel in the mold with a syringe. After the wax material hardened, the mold was removed from the physical model revealing the functional fitting replica denture. The functional fitting replica denture was formed having actual denture teeth partially embedded in wax in the gap on the upper and lower portions of the physical model. The portion of the gap not filled by the denture teeth was substantially filled with the wax which abutted the flat ridge. The crown of the denture teeth was not embedded in the wax. The wax was a pink or flesh color resembling the color of a patient's gingiva, and had gingival features unique to the patient that were replicated by the mold. The gingival structures of the patient, replicated in the wax, formed a gingival architecture made of the formable material. The side of the tooth opposite the occlusal surface, was adjacent the substantially flat, planar ridge with a wax layer between the top surface of the denture teeth and the printed ridge. The position and orientation of the teeth was substantially similar to the position of the teeth of the printed model and the virtual denture design. The denture teeth were held in place adjacent the flat ridge by the wax.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It will be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

We claim:

1. A method of making a functional fitting replica denture for an edentulous patient comprising
    obtaining a virtual three-dimensional (3D) representation of a patient's oral anatomy;
    selecting a virtual denture teeth design having a teeth set prearranged in a fixed position in an occlusal scheme from a plurality of pre-designed virtual denture teeth designs,
        wherein the plurality of pre-designed virtual denture teeth designs comprise a plurality of teeth sets prearranged in a plurality of fixed arch shapes and a plurality of fixed arch sizes, and wherein the arch shapes and arch sizes of the pre-designed virtual denture teeth designs are not modifiable,
    virtually applying the virtual denture teeth design to the virtual 3D representation of a patient's oral anatomy;
    virtually aligning the virtual denture teeth design and the virtual 3D representation to generate a virtual denture; and
    manufacturing a functional fitting replica denture corresponding to the virtual denture.

2. The method of claim 1, wherein the virtual 3D representation of the patient's oral anatomy and the virtual denture teeth design are computer generated 3D representations.

3. The method of claim 1, comprising scanning a portion of the patient's oral anatomy to obtain the virtual 3D representation of the patient's anatomy.

4. The method of claim 1, wherein the step of obtaining a virtual 3D representation of the patient's oral anatomy comprises retrieving a digital data file corresponding to the patient's oral anatomy from the memory of a computing system.

5. The method of claim 1, comprising selecting a virtual denture teeth design having a specific arch size and a specific arch shape that corresponds to the patient's oral anatomy.

6. The method of claim 1, wherein the step of selecting the virtual denture teeth design comprises retrieving a digital data file corresponding to the virtual denture teeth design from the memory of a computing system.

7. The method of claim 1, wherein the method comprises generating a virtual gingiva from a virtual gingiva boundary line that connects points located on at least two virtual teeth of the virtual denture teeth design.

8. The method of claim 1, wherein the plurality of virtual denture teeth designs comprises virtual teeth sets prearranged in fixed positions having occlusal schemes that correspond to arch shapes selected from ovoid, tapering and square arch shapes.

9. The method of claim 1, wherein the plurality of virtual denture teeth designs comprises virtual teeth sets prearranged in fixed orientations selected from ideal, masculine and feminine arrangements.

10. The method of claim 1, comprising obtaining a digital data file of the virtual denture for use an automated manufacturing system to manufacture the virtual denture.

11. The method of claim 1, wherein the functional fitting replica denture is manufactured by an additive manufacturing process.

12. The method of claim 1, wherein the functional fitting replica denture is manufactured by a 3D printing process.

13. The method of claim 1, comprising recording and storing information relating to the virtual denture.

14. The method of claim 1, comprising creating a plurality of pre-designed virtual denture teeth designs by scanning pre-designed denture set-ups to form digital data files of the pre-designed denture set-ups.

15. A computing system comprising
    a processor, a memory and executable instructions stored in the memory which can be executed by the processor to cause a computing system to perform a method comprising
    making a functional fitting replica denture for an edentulous patient comprising obtaining a virtual three-dimensional (3D) representation of a patient's oral anatomy from the memory;
    selecting a virtual denture teeth design having a teeth set that is prearranged in a fixed position in an occlusal scheme corresponding to an arch shape and an arch size, from a plurality of pre-designed virtual denture teeth designs, from the memory, wherein the arch shape and arch size of the pre-designed virtual denture teeth designs are not modifiable;
    executing the executable instructions to virtually apply the virtual denture teeth design to the virtual 3D representation of a patient's anatomy, and virtually align the virtual denture teeth design and the virtual 3D representation to generate a virtual denture stored as a digital data file; and
    manufacturing a functional fitting replica denture corresponding to the virtual denture by an automated manufacturing process.

16. The computing system of claim 15, comprising an automated manufacturing system for manufacturing the functional fitting replica denture that is connected to the computer system by a network interface.

17. The computing system of claim 15, comprising transmitting a digital data file of the virtual denture to an automated manufacturing system to manufacture the functional fitting replica denture.

18. A method of making a functional fitting replica denture for an edentulous patient comprising
- obtaining a virtual three-dimensional representation of a patient's oral anatomy;
- selecting a virtual denture teeth design having a teeth set that is prearranged in a fixed position in an occlusal scheme corresponding to an arch shape and arch size that corresponds with the patient's oral anatomy, wherein the arch shape and arch size is not modifiable;
- virtually aligning the virtual denture teeth design and the virtual three-dimensional representation of a patient's anatomy, and virtually forming a gingival region between the virtual denture teeth design and the virtual 3D representation of the patient's anatomy to generate a virtual denture;
- manufacturing a functional fitting replica denture corresponding to the virtual denture by a 3D printing process to form a physical model of a denture;
- forming a mold of a portion of the physical model that comprises recesses corresponding to a teeth region;
- removing at least a portion of the physical model corresponding to a teeth region;
- placing denture teeth in the recesses of the mold and assembling the mold and the physical model;
- introducing a formable material into the mold to hold the denture teeth in a position on the physical model that corresponds to the virtual design; and
- removing the mold to form the functional fitting replica denture.

19. The method of claim 18, wherein the functional fitting replica denture is used as a try-in denture.

* * * * *